US009255236B2

(12) United States Patent
Grabarse et al.

(10) Patent No.: US 9,255,236 B2
(45) Date of Patent: Feb. 9, 2016

(54) ACID-FREE QUATERNIZED NITROGEN COMPOUNDS AND USE THEREOF AS ADDITIVES IN FUELS AND LUBRICANTS

(71) Applicant: BASF SE, Ludwigshafen (DE)

(72) Inventors: Wolfgang Grabarse, Mannheim (DE); Harald Boehnke, Mannheim (DE); Christian Tock, Alzingen (LU); Cornelia Roeger-Goepfert, Schwetzingen (DE); Ludwig Voelkel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/337,307

(22) Filed: Jul. 22, 2014

(65) Prior Publication Data

US 2014/0331550 A1 Nov. 13, 2014

Related U.S. Application Data

(62) Division of application No. 13/177,042, filed on Jul. 6, 2011, now abandoned.

(60) Provisional application No. 61/485,196, filed on May 12, 2011, provisional application No. 61/361,572, filed on Jul. 6, 2010.

(51) Int. Cl.

| | |
|---|---|
| ***C10L 10/04*** | (2006.01) |
| ***C10L 1/2383*** | (2006.01) |
| ***C10L 1/2387*** | (2006.01) |
| ***C10L 10/00*** | (2006.01) |
| ***C10L 10/14*** | (2006.01) |
| ***C10L 10/18*** | (2006.01) |
| ***C10M 133/16*** | (2006.01) |
| ***C10M 133/56*** | (2006.01) |
| *C10L 1/224* | (2006.01) |
| *C10L 1/222* | (2006.01) |

(52) U.S. Cl.

CPC ............... *C10L 10/04* (2013.01); *C10L 1/2383* (2013.01); *C10L 1/2387* (2013.01); *C10L 10/00* (2013.01); *C10L 10/14* (2013.01); *C10L 10/18* (2013.01); *C10M 133/16* (2013.01); *C10M 133/56* (2013.01); *C10L 1/224* (2013.01); *C10L 1/2222* (2013.01); *C10L 2230/22* (2013.01); *C10M 2203/1045* (2013.01); *C10M 2215/28* (2013.01); *C10N 2220/021* (2013.01); *C10N 2230/04* (2013.01); *C10N 2240/10* (2013.01)

(58) Field of Classification Search

CPC ...................................................... C10L 10/04

See application file for complete search history.

(56) References Cited

U.S. PATENT DOCUMENTS

| | | | | |
|---|---|---|---|---|
| 2,901,430 | A | 8/1959 | Chiddix | |
| 3,215,707 | A | 11/1965 | Rense | |
| 3,259,578 | A | 7/1966 | Dickson | |
| 3,962,104 | A | 6/1976 | Swietlik et al. | |
| 4,179,424 | A | 12/1979 | Phillips et al. | |
| 4,248,719 | A | 2/1981 | Chafetz et al. | |
| 4,253,980 | A | 3/1981 | Hammond et al. | |
| 4,326,973 | A | 4/1982 | Hammond | |
| 4,438,045 | A * | 3/1984 | Nieh et al. | 560/193 |
| 4,564,372 | A | 1/1986 | Campbell | |
| 4,581,151 | A | 4/1986 | Campbell | |
| 4,600,409 | A | 7/1986 | Campbell | |
| 4,612,132 | A | 9/1986 | Wollenberg | |
| 7,947,093 | B2 | 5/2011 | Barton et al. | |
| 7,951,211 | B2 | 5/2011 | Barton | |
| 8,147,569 | B2 | 4/2012 | Barton | |
| 8,153,570 | B2 | 4/2012 | Barton | |
| 8,476,207 | B2 | 7/2013 | Barton | |
| 8,961,623 | B2 | 2/2015 | Stevenson | |
| 2004/0154216 | A1 | 8/2004 | Huffer et al. | |
| 2005/0081432 | A1 | 4/2005 | Panchalingam et al. | |
| 2007/0015681 | A1 | 1/2007 | Allef et al. | |
| 2007/0155636 | A1 | 7/2007 | Koishikawa | |

(Continued)

FOREIGN PATENT DOCUMENTS

| | | | |
|---|---|---|---|
| DE | 100 19 142 | A1 | 10/2001 |
| EP | 0 293 192 | A1 | 11/1988 |

(Continued)

OTHER PUBLICATIONS

Gen Sugiyama, et al., "Oxidation Degradation and Acid Generation in Diesel Fuel Containing 5% FAME", SAE International, Technical Paper, Product-code: 2007-01-2027, Jul. 23, 2007, pp. 1243-1253.

(Continued)

*Primary Examiner* — Yong Chu

(74) *Attorney, Agent, or Firm* — Oblon, McClelland, Maier & Neustadt, L.L.P.

(57) ABSTRACT

The present invention relates to novel acid-free quaternized nitrogen compounds, to the preparation thereof and to the use thereof as a fuel and lubricant additive, more particularly as a detergent additive, as a wax antisettling additive (WASA) or as an additive for reducing internal diesel injector deposits (IDID); to additive packages which comprise these compounds; and to fuels and lubricants thus additized. The present invention further relates to the use of these acid-free quaternized nitrogen compounds as a fuel additive for reducing or preventing deposits in the injection systems of direct-injection diesel engines, especially in common-rail injection systems, for reducing the fuel consumption of direct-injection diesel engines, especially of diesel engines with common-rail injection systems, and for minimizing power loss in direct-injection diesel engines, especially in diesel engines with common-rail injection systems.

16 Claims, 1 Drawing Sheet

(56) References Cited

U.S. PATENT DOCUMENTS

| | | | |
|---|---|---|---|
| 2008/0307698 A1 | 12/2008 | Barton et al. | |
| 2010/0006049 A1 | 1/2010 | Jung et al. | |
| 2010/0257779 A1 | 10/2010 | Barton et al. | |
| 2010/0293844 A1 | 11/2010 | MacMillan | |
| 2011/0048354 A1 | 3/2011 | Hollingshurst | |
| 2011/0160594 A1 | 6/2011 | Platsch et al. | |
| 2011/0245391 A1 | 10/2011 | Karpov et al. | |
| 2011/0245392 A1 | 10/2011 | Karpov et al. | |
| 2011/0258917 A1 | 10/2011 | Castro et al. | |
| 2011/0290659 A1 | 12/2011 | Roeger-Göpfert et al. | |
| 2012/0138004 A1 | 6/2012 | Stevenson et al. | |
| 2013/0225463 A1* | 8/2013 | Hansch et al. | 508/547 |

FOREIGN PATENT DOCUMENTS

| | | | |
|---|---|---|---|
| EP | 0 391 735 A1 | 10/1990 | |
| EP | 0 538 819 A2 | 4/1993 | |
| GB | 1445993 | 8/1976 | |
| WO | WO 2005024096 A1 * | 3/2005 | |
| WO | 2006/135881 A2 | 12/2006 | |
| WO | WO 2006/135881 A2 | 12/2006 | |
| WO | WO 2007/045386 A1 | 4/2007 | |
| WO | WO 2007/128740 A1 | 11/2007 | |
| WO | WO 2008/144097 A1 | 11/2008 | |
| WO | 2009/040586 A1 | 4/2009 | |
| WO | 2009/140190 A1 | 11/2009 | |
| WO | 2010/132259 A1 | 11/2010 | |
| WO | WO 2010/132259 | 11/2010 | |

OTHER PUBLICATIONS

Polybutylene Succinic Anhydrides for FDA prepared by the American Chemistry Council Petroleum Additives Panel Health, Environmental, and Regulatory Task Group, Dec. 2005.

International Search Report issued Aug. 2, 2011.

* cited by examiner

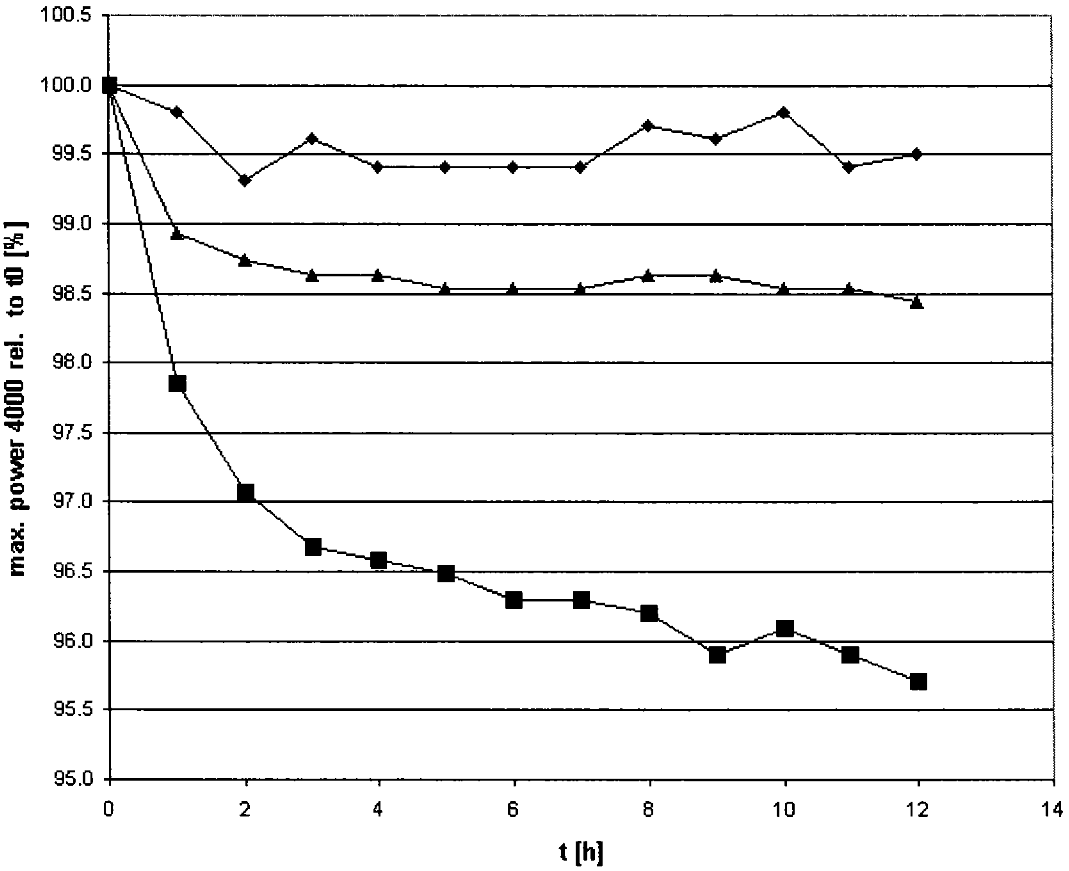
100.5
100.0
99.5
99.0
98.5
98.0
97.5
97.0
96.5
96.0
95.5
95.0
max. power 4000 rel. to t0 [%]
0
2
4
6
8
10
12
14
t [h]

ACID-FREE QUATERNIZED NITROGEN COMPOUNDS AND USE THEREOF AS ADDITIVES IN FUELS AND LUBRICANTS

This application is a Division of U.S. application Ser. No. 13/177,042, filed Jul. 6, 2011, now abandoned; and claims benefit of U.S. provisional application Ser. No. 61/485,196, filed May 12, 2011; and of U.S. provisional application Ser. No. 61/361,572, filed Jul. 6, 2010, all incorporated herein by reference.

The present invention relates to novel acid-free quaternized nitrogen compounds, to the preparation thereof and to the use thereof as a fuel and lubricant additive, more particularly as a detergent additive, as a wax antisettling additive (WASA) or as an additive for reducing internal diesel injector deposits (IDID); to additive packages which comprise these compounds; and to fuels and lubricants thus additized. The present invention further relates to the use of these acid-free quaternized nitrogen compounds as a fuel additive for reducing or preventing deposits in the injection systems of direct-injection diesel engines, especially in common-rail injection systems, for reducing the fuel consumption of direct-injection diesel engines, especially of diesel engines with common-rail injection systems, and for minimizing power loss in direct-injection diesel engines, especially in diesel engines with common-rail injection systems.

STATE OF THE ART

In direct-injection diesel engines, the fuel is injected and distributed ultrafinely (nebulized) by a multihole injection nozzle which reaches directly into the combustion chamber in the engine, instead of being introduced into a prechamber or swirl chamber as in the case of the conventional (chamber) diesel engine. The advantage of the direct-injection diesel engines lies in their high performance for diesel engines and nevertheless low fuel consumption. Moreover, these engines achieve a very high torque even at low speeds.

At present, essentially three methods are being used to inject the fuel directly into the combustion chamber of the diesel engine: the conventional distributor injection pump, the pump-nozzle system (unit-injector system or unit-pump system) and the common-rail system.

In the common-rail system, the diesel fuel is conveyed by a pump with pressures up to 2000 bar into a high-pressure line, the common rail. Proceeding from the common rail, branch lines run to the different injectors which inject the fuel directly into the combustion chamber. The full pressure is always applied to the common rail, which enables multiple injection or a specific injection form. In the other injection systems, in contrast, only smaller variation in the injection is possible. The injection in the common rail is divided essentially into three groups: (1.) pre-injection, by which essentially softer combustion is achieved, such that harsh combustion noises ("nailing") are reduced and the engine seems to run quietly; (2.) main injection, which is responsible especially for a good torque profile; and (3.) post-injection, which especially ensures a low NO value. In this post-injection, the fuel is generally not combusted, but instead evaporated by residual heat in the cylinder. The exhaust gas/fuel mixture formed is transported to the exhaust gas system, where the fuel, in the presence of suitable catalysts, acts as a reducing agent for the nitrogen oxides $NO_x$.

The variable, cylinder-individual injection in the common-rail injection system can positively influence the pollutant emission of the engine, for example the emission of nitrogen oxides ($NO_x$), carbon monoxide (CO) and especially of particulates (soot). This makes it possible, for example, that engines equipped with common-rail injection systems can meet the Euro 4 standard theoretically even without additional particulate filters.

In modern common-rail diesel engines, under particular conditions, for example when biodiesel-containing fuels or fuels with metal impurities such as zinc compounds, copper compounds, lead compounds and other metal compounds are used, deposits can form on the injector orifices, which adversely affect the injection performance of the fuel and hence impair the performance of the engine, i.e. especially reduce the power, but in some cases also worsen the combustion. The formation of deposits is enhanced further by further developments in the injector construction, especially by the change in the geometry of the nozzles (narrower, conical orifices with rounded outlet). For lasting optimal functioning of engine and injectors, such deposits in the nozzle orifices must be prevented or reduced by suitable fuel additives.

WO 2006/135881 describes quaternized ammonium salts prepared by condensation of a hydrocarbyl-substituted acylating agent and of an oxygen- or nitrogen-containing compound with a tertiary amino group, and subsequent quaternization by means of hydrocarbyl epoxide in the presence of stoichiometric amounts of an acid, especially acetic acid. Stoichiometric amounts of the acid are required to ensure complete ring opening of the epoxide quaternizing agent and hence very substantially quantitative quaternization. The reaction of a dicarboxylic acid-based acylating agent, such as the PIBSA used in the examples therein, with an amine, such as dimethylaminopropylamine (DMAPA), under condensation conditions, i.e. elimination of water, forms a DMAPA succinimide which is then quaternized with epoxide and acid in equimolar amounts in each case.

Following the technical teaching of WO 2006/135881, the presence of the stoichiometric amounts of acid, which is additionally absolutely necessary to balance the charge for the quaternized imide detergent therein, is found to be particularly disadvantageous. In order to reduce the acid content of the imide therein, or in order to entirely remove acid, additional process measures would be required, which would make the preparation of the product more complex and hence would make it much more expensive. The epoxide-quaternized imide prepared according to WO 2006/135881 is therefore—without further purification—used in the form of the carboxylate salt as a fuel additive in the tests described in the application.

On the other hand, however, it is known that acids can cause corrosion problems in fuel additives (cf., for example, Sugiyama et al; SAE International, Technical Paper, Product Code: 2007-01-2027, Date Published: Jul. 23, 2007). The epoxide-quaternized additive provided according to WO 2006/135881 is therefore afflicted with significant application risks a priori owing to the considerable corrosion risk which exists. Furthermore, the product has distinct disadvantages with regard to motor oil compatibility and low-temperature properties.

In the injection systems of modern diesel engines, deposits cause significant performance problems. It is common knowledge that such deposits in the spray channels can lead to a decrease in the fuel flow and hence to power loss. Deposits at the injector tip, in contrast, impair the optimal formation of fuel spray mist and, as a result, cause worsened combustion and associated higher emissions and increased fuel consumption. In contrast to these conventional "external" deposition phenomena, "internal" deposits (referred to collectively as internal diesel injector deposits (IDID)) in particular parts of the injectors, such as at the nozzle needle, at the control piston, at the valve piston, at the valve seat, in the control unit and in the guides of these components, also increasingly cause performance problems. Conventional additives exhibit inadequate action against these IDIDs.

It is therefore an object of the present invention to provide improved quaternized fuel additives, especially based on hydrocarbyl-substituted polycarboxylic anhydrides, which no longer have the disadvantages of the prior art mentioned.

BRIEF DESCRIPTION OF THE INVENTION

It has now been found that, surprisingly, the above object is achieved by providing an addition process, performable under acid-free conditions, for preparing epoxide-quaternized nitrogen-containing additives based on hydrocarbyl-substituted polycarboxylic anhydrides and compounds which have quaternizable amino groups and are reactive therewith, and by the acid-free reaction products thus obtainable.

The inventive reaction regime surprisingly allows the addition of free acid to be dispensed with completely, especially of free protic acid which, according to the prior art, necessarily has to be added to the alkylene oxide quaternizing reagent. This is because the inventive process regime, by virtue of addition of the nitrogen-containing quaternizable compound onto the hydrocarbyl-substituted polycarboxylic anhydride and opening of the anhydride ring, generates an intramolecularly bound acid function, and it is assumed that, without being bound to this model consideration, that this intramolecularly generated carboxyl group activates the alkylene oxide in the quaternization reaction and, by protonation of the intermediate alcohol which forms after the addition of the alkylene oxide, forms the reaction product in the form of a betaine structure.

Surprisingly, the inventive additives thus prepared are superior in several respects to the prior art additives prepared in a conventional manner by epoxide/acid quaternization.

DESCRIPTION OF FIGURES

FIG. 1 shows the power loss of different diesel fuels in a DW10 engine test. In particular, this is shown for unadditized fuel (squares) and a fuel additized in accordance with the invention (rhombuses), compared to a comparative fuel admixed with prior art additive at the same dosage (triangles).

DETAILED DESCRIPTION OF THE INVENTION

A1) Specific Embodiments

The present invention relates especially to the following specific embodiments:

1. A process for preparing quaternized nitrogen compounds, wherein
    a. a compound comprising at least one oxygen- or nitrogen-containing group reactive with the anhydride, for example an —OH and/or a primary or secondary amino group, and additionally comprising at least one quaternizable amino group is added onto a polycarboxylic anhydride compound, especially a polycarboxylic anhydride or a hydrocarbyl-substituted polycarboxylic anhydride, especially a polyalkylene-substituted polycarboxylic anhydride, and
    b. the product from stage a) is quaternized with an especially $H^+$ donor-free and in particular acid-free quaternizing agent.
2. The process according to embodiment 1, wherein the polycarboxylic anhydride compound is a di-, tri- or tetracarboxylic anhydride.
3. The process according to either of the preceding embodiments, wherein the polycarboxylic anhydride compound is the anhydride of a $C_4$-$C_{10}$-dicarboxylic acid.
4. The process according to any of the preceding embodiments, wherein the polycarboxylic anhydride compound comprises at least one high molecular weight hydrocarbyl substituent, especially polyalkylene substituent, having a number-average molecular weight (Mn) in the range from about 200 to 10 000, for example 300 to 8000, especially 350 to 5000.
5. The process according to any of the preceding embodiments, wherein the compound reactive with the anhydride is selected from
    a. mono- or polyamines which are substituted by low molecular weight hydroxyhydrocarbyl, especially low molecular weight hydroxyalkyl, and have at least one quaternizable primary, secondary or tertiary amino group;
    b. straight-chain or branched, cyclic, heterocyclic, aromatic or nonaromatic polyamines having at least one primary or secondary (anhydride-reactive) amino group and having at least one quaternizable primary, secondary or tertiary amino group;
    c. piperazines.
6. The process according to embodiment 5, wherein the compound reactive with the anhydride is selected from
    a. primary, secondary or tertiary monoamines substituted by low molecular weight hydroxyhydrocarbyl, especially low molecular weight hydroxyalkyl, and hydroxyalkyl-substituted primary, secondary or tertiary diamines,
    b. straight-chain or branched aliphatic diamines having two primary amino groups; di- or polyamines having at least one primary and at least one secondary amino group; di- or polyamines having at least one primary and at least one tertiary amino group; aromatic carbocyclic diamines having two primary amino groups; aromatic heterocyclic polyamines having two primary amino groups; aromatic or nonaromatic heterocycles having one primary and one tertiary amino group.
7. The process according to any of the preceding embodiments, wherein the quaternizing agent is selected from epoxides, especially hydrocarbyl-substituted epoxides.
8. The process according to embodiment 7, wherein the quaternization is effected without addition of an $H^+$ donor, especially without addition of acid.
9. The process according to any of the preceding embodiments, wherein stage a), i.e. the addition reaction, is performed at a temperature of less than about 80° C. and especially at a temperature in the range from about 30 to 70° C., in particular 40 to 60° C.
10. The process according to any of the preceding embodiments, wherein stage a) is performed over a period of 1 minute to 10 hours or 10 minutes to 5 hours or 10 minutes to 4 hours or 2 to 3 hours.
11. The process according to any of the preceding embodiments, wherein stage b), i.e. the quaternization, is performed at a temperature in the range from 40 to 80° C.
12. The process according to any of the preceding embodiments, wherein stage b) is performed over a period of 1 to 10 hours.
13. The process according to any of the preceding embodiments, wherein stage b) is performed with an epoxide, especially low molecular weight hydrocarbyl epoxide, as the quaternizing agent in the absence of (stoichiometric amounts of) free acid (other than the polycarboxylic acid compound).

14. The process according to any of the preceding embodiments, wherein the reaction according to stage a) and/or b) is effected in the absence of a solvent, in particular in the absence of an organic protic solvent.

15. A quaternized nitrogen compound or reaction product obtainable by a process according to any of the preceding embodiments.

16. A quaternized nitrogen compound or reaction product according to embodiment 15, comprising at least one compound of the general formulae:

(Ia-1)

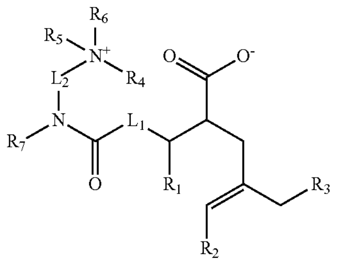

(Ia-2)

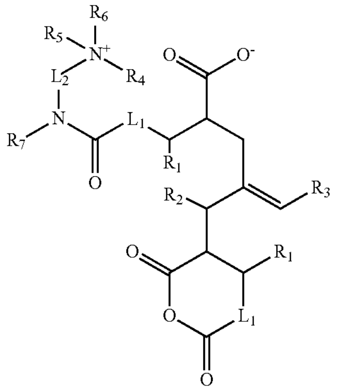

(Ia-3)

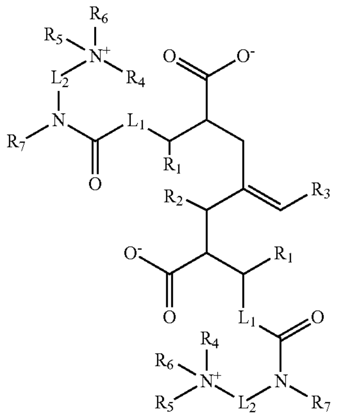

especially Ia-1, optionally in combination with Ia-2 and/or Ia-3, or (Ib-1)

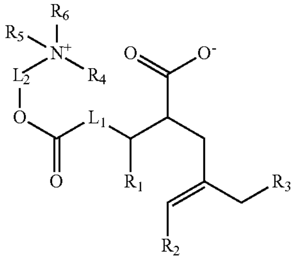

(Ib-2)

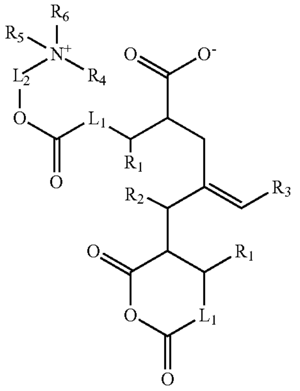

(Ib-3)

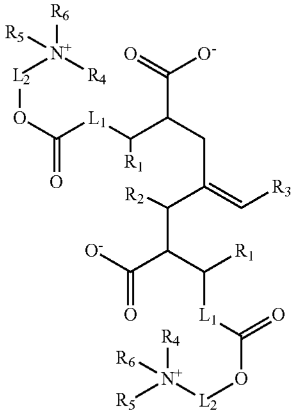

especially Ib-1, optionally in combination with Ib-2 and/or Ib-3, in which $R_1$ is H or a straight-chain or branched hydrocarbyl radical which may optionally be mono- or polysubstituted by hydroxyl, carboxyl, hydrocarbyloxy and/or acyl radicals, or has one or more ether groups in the hydrocarbyl chain, and is especially H or short-chain hydrocarbyl, especially alkyl;

$R_2$ is H or alkyl; $R_3$ is hydrocarbyl, especially long-chain hydrocarbyl, for example a polyalkylene radical;

at least one of the $R_4$, $R_5$ and $R_6$ radicals is a radical introduced by quaternization, especially a low molecular weight hydrocarbyl radical or low molecular weight hydroxyl-substituted hydrocarbyl radical, and the remaining radicals are selected from straight-chain or branched low molecular weight hydrocarbyl radicals, cyclic hydrocarbyl radicals, which are optionally mono- or polysubstituted and/or have one or more heteroatoms;

$R_7$ is H or a straight-chain or branched low molecular weight hydrocarbyl radical which may optionally be mono- or polysubstituted, for example di-, tri- or tetrasubstituted, by identical or different hydroxyl, carboxyl, low molecular weight hydrocarbyloxy and/or acyl radicals, or has one or more ether groups in the hydrocarbyl chain, or $R_7$ together with one of the $R_4$, $R_5$ and $R_6$ radicals forms a bridge group, for example an alkylene or alkenylene group;

$L_1$ is a chemical bond or a straight-chain or branched alkylene group and $L_2$ is a straight-chain or branched alkylene group which optionally bears one or more heteroatoms, especially selected from —O— and —NH—, or substituents.

17. A quaternized nitrogen compound or reaction product according to embodiment 15 or 16 which is essentially $H^+$ donor-free, especially essentially acid-free, and especially comprises no inorganic acids or short-chain organic acids.
18. The use of a quaternized nitrogen compound or of a reaction product according to any of embodiments 15 to 17 as a fuel additive or lubricant additive.
19. The use according to embodiment 18 as a detergent additive for diesel fuels.
20. The use according to embodiment 18 as a wax antisettling additive (WASA) for middle distillate fuels, especially diesel fuels.
21. The use according to embodiment 19 as an additive for reducing or preventing deposits in injection systems of direct-injection diesel engines, especially in common-rail injection systems, for reducing the fuel consumption of direct-injection diesel engines, especially of diesel engines with common-rail injection systems, and/or for minimizing power loss in direct-injection diesel engines, especially in diesel engines with common-rail injection systems.
22. The use according to embodiment 21 as an additive for controlling (preventing or reducing, especially partly, essentially completely or completely reducing) internal diesel engine deposits (IDID), i.e. deposits in the interior of the injector; especially wax or soap-like deposits and/or carbon-like polymeric deposits.
23. An additive concentrate comprising, in combination with further fuel additives, especially diesel fuel additives, at least one quaternized nitrogen compound or a reaction product according to any of embodiments 15 and 16.
24. A fuel composition comprising, in a majority of a customary base fuel, a (detergency-)effective amount of at least one quaternized nitrogen compound or of a reaction product according to either of embodiments 15 and 16.
25. A lubricant composition comprising, in a majority of a customary lubricant, a (detergency-)effective amount of at least one quaternized nitrogen compound or of a reaction product according to either of embodiments 15 and 16.

A2) General Definitions

An "$H^+$ donor" or "proton donor" refers to any chemical compound which is capable of releasing a proton to a proton acceptor. Examples are especially protic acids, but also water.

"Acid-free" in the context of the present invention means the absence of low molecular weight inorganic or organic acid and/or of the corresponding anion thereof, and includes both the lack of addition of acid during the preparation process according to the invention and, more particularly, the absence of acid and/or of the anion thereof in the quaternized reaction product used as the additive. Freedom from acid includes especially the absence of stoichiometric amounts of such acids and anions thereof (stoichiometry based on the quaternizing agent used, such as especially the epoxide), and exists especially when, based on epoxide quaternizing agent used, free acid or anion thereof is present only in substoichiometric amounts, for example in molar ratios of less than 1:0.1, or less than 1:0.01 or 1:0.001, or 1:0.0001, of quaternizing agent to acid. Freedom from acid especially also includes the complete absence of an inorganic or organic protic acid and/or anion thereof (i.e. when protic acid and/or the anion thereof is analytically no longer detectable). An "acid" in this context is especially a free protic acid.

Examples of typical "protic acids" include inorganic acids or mineral acids, such as HCl, $H_2SO_4$, $HNO_3$, $H_2CO_3$, and organic carboxylic acids, especially monocarboxylic acids of the RCOOH type in which R is a short-chain hydrocarbyl radical.

"Free" or "unbound" acid means that the acid function is not part of a quaternized compound itself, i.e. is in principle removable from the quaternized compound, for example by ion exchange.

Typical "anions" of protic acids are, for example, carboxylate anions, for example acetate and propionate.

"Quaternizable" nitrogen groups or amino groups include especially primary, secondary and tertiary amino groups.

A "condensation" or "condensation reaction" in the context of the present invention describes the reaction of two molecules with elimination of a relatively small molecule, especially of a water molecule. When such an elimination is not detectable, more particularly not detectable in stoichiometric amounts, and the two molecules react nevertheless, for example with addition, the reaction in question of the two molecules is "without condensation".

A "betaine" refers to a specific salt form of a chemical compound which has both a negative charge and a positive charge in one and the same molecule, wherein the charge, however, cannot be eliminated by intramolecular ion transfer.

"IDID" stands for "internal diesel injector deposits", as observed in modern diesel engines. While conventional (external) deposits are coke-like deposits in the region of the needle tips and the spray holes of the injection nozzles, there is in the meantime an accumulation of deposits in the interior of the injection nozzles, which lead to significant performance problems, for example blockage of the internal moving parts of the valve and associated worsening or lack of control of fuel injection, power loss and the like. The IDIDs occur either in the form of wax- or soap-like deposits (fatty acid residues and/or $C_{12}$- or $C_{16}$-alkyl succinic acid residues detectable analytically) or in the form of polymeric carbon deposits. The latter in particular make particular demands with regard to the removal/avoidance thereof.

In the absence of statements to the contrary, the following general conditions apply:

"Hydrocarbyl" can be interpreted widely and comprises both long-chain and short-chain, straight-chain and branched hydrocarbon radicals, which may optionally additionally comprise heteroatoms, for example O, N, NH, S, in the chain thereof.

"Cyclic hydrocarbyl radicals" may comprise aromatic or nonaromatic rings and optionally have one or more ring heteroatoms selected from O, S, N, NH.

"Long-chain" or "high molecular weight" hydrocarbyl radicals have a number-average molecular weight ($M_n$) of 85 to 20 000, for example 113 to 10 000, or 200 to 10 000 or 350 to 5000, for example 350 to 3000, 500 to 2500, 700 to 2500, or 800 to 1500. More particularly, they are formed essentially from $C_{2-6}$, especially $C_{2-4}$, monomer units such as ethylene, propylene, n- or isobutylene or mixtures thereof, where the different monomers may be copolymerized in random distribution or as blocks. Such long-chain hydrocarbyl radicals are also referred to as polyalkylene radicals or poly-$C_{2-6}$- or poly-$C_{2-4}$-alkylene radicals. Suitable long-chain hydrocarbyl radicals and the preparation thereof are also described, for example, in WO 2006/135881 and the literature cited therein.

Examples of particularly useful polyalkylene radicals are polyisobutenyl radicals derived from "high-reactivity" polyisobutenes which are notable for a high content of terminal double bonds. Terminal double bonds are alpha-olefinic double bonds of the type

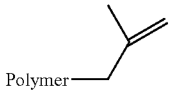

which are also referred to collectively as vinylidene double bonds. Suitable high-reactivity polyisobutenes are, for example, polyisobutenes which have a proportion of vinylidene double bonds of greater than 70 mol %, especially greater than 80 mol % or greater than 85 mol %. Preference is given especially to polyisobutenes which have homogeneous polymer structures. Homogeneous polymer structures are possessed especially by those polyisobutenes formed from isobutene units to an extent of at least 85% by weight, preferably to an extent of at least 90% by weight and more preferably to an extent of at least 95% by weight. Such high-reactivity polyisobutenes preferably have a number-average molecular weight within the abovementioned range. In addition, the high-reactivity polyisobutenes may have a polydispersity in the range from 1.05 to 7, especially of about 1.1 to 2.5, for example of less than 1.9 or less than 1.5. Polydispersity is understood to mean the quotient of weight-average molecular weight Mw divided by the number-average molecular weight Mn.

Particularly suitable high-reactivity polyisobutenes are, for example, the Glissopal brands from BASF SE, especially Glissopal 1000 (Mn=1000), Glissopal V 33 (Mn=550) and Glissopal 2300 (Mn=2300), and mixtures thereof. Other number-average molecular weights can be established in a manner known in principle by mixing polyisobutenes of different number-average molecular weights or by extractive enrichment of polyisobutenes of particular molecular weight ranges.

"Short-chain hydrocarbyl" or "low molecular weight hydrocarbyl" is especially straight-chain or branched alkyl or alkenyl, optionally interrupted by one or more, for example 2, 3 or 4, heteroatom groups such as —O— or —NH—, or optionally mono- or polysubstituted, for example di-, tri- or tetrasubstituted.

"Short-chain hydrocarbyloxy" or "low molecular weight hydrocarbyloxy" is especially straight-chain or branched alkyloxy or alkenyloxy, optionally interrupted by one or more, for example 2, 3 or 4, heteroatom groups such as —O— or —NH—, or optionally mono- or polysubstituted, for example di-, tri- or tetrasubstituted.

"Hydroxyl-substituted hydrocarbyl" or "hydroxyhydrocarbyl" represents especially the hydroxyl-substituted analogs of the alkyl or alkenyl radicals defined herein.

"Alkyl" or "lower alkyl" represents especially saturated, straight-chain or branched hydrocarbon radicals having 1 to 4, 1 to 6, 1 to 8, or 1 to 10 or 1 to 20, carbon atoms, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; and also n-heptyl, n-octyl, n-nonyl and n-decyl, and the singly or multiply branched analogs thereof.

"Hydroxyalkyl" represents especially the mono- or polyhydroxylated, especially monohydroxylated, analogs of the above alkyl radicals, for example the monohydroxylated analogs of the above straight-chain or branched alkyl radicals, for example the linear hydroxyalkyl groups with a primary hydroxyl group, such as hydroxymethyl, 2-hydroxyethyl, 3-hydroxypropyl, 4-hydroxybutyl.

"Alkenyl" represents mono- or polyunsaturated, especially monounsaturated, straight-chain or branched hydrocarbon radicals having 2 to 4, 2 to 6, 2 to 8, 2 to 10 or 2 to 20 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Hydroxyalkenyl" represents especially the mono- or polyhydroxylated, especially monohydroxylated, analogs of the above alkenyl radicals.

"Alkyloxy" and "alkenyloxy" represent especially the oxygen-bonded analogs of the above "alkyl" and "alkenyl" radicals.

"Alkylene" represents straight-chain or mono- or polybranched hydrocarbon bridge groups having 1 to 10 carbon atoms, for example $C_1$-$C_7$-alkylene groups selected from $—CH_2—$, $—(CH_2)_2—$, $—(CH_2)_3—$, $—(CH_2)_4—$, $—(CH_2)_2—CH(CH_3)—$, $—CH_2—CH(CH_3)—CH_2—$, $(CH_2)_4—$, $—(CH_2)_5—$, $—(CH_2)_6$, $—(CH_2)_7—$, $—CH(CH_3)—CH_2—CH_2—CH(CH_3)—$ or $—CH(CH_3)—CH_2—CH_2—CH_2—CH(CH_3)—$ or $C_1$-$C_4$-alkylene groups selected from $—CH_2—$, $—(CH_2)_2—$, $—(CH_2)_3—$, $—(CH_2)_4—$, $—(CH_2)_2—CH(CH_3)—$, $—CH_2—CH(CH_3)—CH_2$; or $C_2$-$C_6$-alkylene groups, as for example $—CH_2—CH(CH_3)—$, $—CH(CH_3)—CH_2—$, $—CH(CH_3)—CH(CH_3)—$, $—C(CH_3)_2—CH_2—$, $—CH_2—C(CH_3)_2—$, $—C(CH_3)_2—CH(CH_3)—$, $—CH(CH_3)—C(CH_3)_2—$, $—CH_2—CH(CH_2CH_3)—$, $—CH(CH_2CH_3)—CH_2—$, $—CH(CH_2CH_3)—CH(CH_2CH_3)—$, $—C(CH_2CH_3)_2—CH_2—$, $—CH_2—C(CH_2CH_3)_2—$, $—CH_2—CH$(n-propyl)-, $—CH$(n-propyl)-$CH_2—$, $—CH$(n-propyl)-$CH(CH_3)—$, $—CH_2—$ CH(n-butyl)-, —CH(n-butyl)-$CH_2$—, —$CH(CH_3)$—CH($CH_2CH_3$)—, —$CH(CH_3)$—CH(n-propyl)-, —CH($CH_2CH_3$)—$CH(CH_3)$—, —$CH(CH_3)$—CH($CH_2CH_3$)—, or $C_2$-$C_4$-alkylene groups, as for example —$(CH_2)_2$—, —$CH_2$—$CH(CH_3)$—, —$CH(CH_3)$—$CH_2$—, —$CH(CH_3)$—$CH(CH_3)$—, —$C(CH_3)_2$—$CH_2$—, —$CH_2$—$C(CH_3)_2$—, —$CH_2$—CH($CH_2CH_3$)—, —CH($CH_2CH_3$)—$CH_2$—.

"Alkenylene" represents the mono- or polyunsaturated, especially monounsaturated, analogs of the above alkylene groups having 2 to 10 carbon atoms, especially $C_2$-$C_7$-alkenylenes or $C_2$-$C_4$-alkenylenes, such as —CH═CH—, —CH═CH—$CH_2$—, —$CH_2$—CH═CH—, —CH═CH—$CH_2$—$CH_2$—, —$CH_2$—CH═CH—$CH_2$—, —$CH_2$—$CH_2$—CH═CH—, —$CH(CH_3)$—CH═CH—, —$CH_2$—C($CH_3$)═CH—.

"Acyl" represents radicals derived from straight-chain or branched, optionally mono- or polyunsaturated, optionally substituted $C_1$-$C_{24}$, especially $C_1$-$C_{12}$ or $C_1$-$C_8$, monocarboxylic acids. For example, useful acyl radicals are derived from the following carboxylic acids: saturated acids such as formic acid, acetic acid, propionic acid and n- and i-butyric acid, n- and i-valeric acid, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid, behenic acid, lignoceric acid, cerotic acid and melissic acid; monounsaturated acids such as acrylic acid, crotonic acid, palmitoleic acid, oleic acid and erucic acid; and diunsaturated acids such as sorbic acid and linoleic acid. When double bonds are present in the fatty acids, they may either be in cis form or in trans form.

"Cyclic hydrocarbyl radicals" comprise especially:

cycloalkyl: carbocyclic radicals having 3 to 20 carbon atoms, for example $C_3$-$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl, cycloheptyl, and also to cyclopropylmethyl, cyclopropylethyl, cyclobutylmethyl, cyclobutylethyl, cyclopentylmethyl, cyclopentylethyl, cyclohexylmethyl, or $C_3$-$C_7$-cycloalkyl such as cyclopropyl, cyclobutyl, cyclopentyl, cyclohexyl, cycloheptyl, cyclopropylmethyl, cyclopropylethyl, cyclobutylmethyl, cyclopentylethyl, cyclohexylmethyl, where the bond to the rest of the molecule may be via any suitable carbon atom.

cycloalkenyl: monocyclic, monounsaturated hydrocarbon groups having 5 to 8, preferably up to 6, carbon ring members, such as cyclopenten-1-yl, cyclopenten-3-yl, cyclohexen-1-yl, cyclohexen-3-yl and cyclohexen-4-yl;

aryl: mono- or polycyclic, preferably mono- or bicyclic, optionally substituted aromatic radicals having 6 to 20, for example 6 to 10, ring carbon atoms, for example phenyl, biphenyl, naphthyl such as 1- or 2-naphthyl, tetrahydronaphthyl, fluorenyl, indenyl and phenanthrenyl. These aryl radicals may optionally bear 1, 2, 3, 4, 5 or 6 identical or different substituents.

arylalkyl: the aryl-substituted analogs of the above alkyl radicals, where aryl is likewise as defined above, for example phenyl-$C_1$-$C_4$-alkyl radicals selected from phenylmethyl and phenylethyl.

heterocyclyl: five- to seven-membered saturated, partially unsaturated or aromatic (=heteroaryl or hetaryl) heterocycles or heterocyclyl radicals comprising one, two, three or four heteroatoms from the group of O, N and S. For example, the following subgroups may be mentioned:

5- or 6-membered saturated or monounsaturated heterocyclyl comprising one or two nitrogen atoms and/or one oxygen or sulfur atom or one or two oxygen and/or sulfur atoms as ring members, for example 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl and 2-piperazinyl;

5-membered aromatic heterocyclyl comprising, as well as carbon atoms, one, two or three nitrogen atoms or one or two nitrogen atoms and one sulfur or oxygen atom as ring members, for example 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, and 1,3,4-triazol-2-yl;

5-membered aromatic heterocyclyl which has 1, 2, 3 or 4 nitrogen atoms as ring members, such as 1-, 2- or 3-pyrrolyl, 1-, 3- or 4-pyrazolyl, 1-, 2- or 4-imidazolyl, 1,2,3-[1H]triazol-1-yl, 1,2,3-[2H]-triazol-2-yl, 1,2,3-[1H]triazol-4-yl, 1,2,3-[1H]-triazol-5-yl, 1,2,3-[2H]-triazol-4-yl, 1,2,4-[1H]-triazol-1-yl, 1,2,4-[1H]-triazol-3-yl, 1,2,4-[1H]-triazol-5-yl, 1,2,4-[4H]triazol-4-yl, 1,2,4-[4H]triazol-3-yl, [1H]tetrazol-1-yl, [1H]-tetrazol-5-yl, [2H]-tetrazol-2-yl and [2H]-tetrazol-5-yl;

5-membered aromatic heterocyclyl which has 1 heteroatom selected from oxygen and sulfur and optionally 1, 2 or 3 nitrogen atoms as ring members, for example 2-furyl, 3-furyl, 2-thienyl, 3-thienyl, 3- or 4-isoxazolyl, 3- or 4-isothiazolyl, 2-, 4- or 5-oxazolyl, 2-, 4- or 5-thiazolyl, 1,2,4-thiadiazol-3-yl, 1,2,4-thiadiazol-5-yl, 1,3,4-thiadiazol-2-yl, 1,2,4-oxadiazol-3-yl, 1,2,4-oxadiazol-5-yl and 1,3,4-oxadiazol-2-yl;

6-membered heterocyclyl comprising, as well as carbon atoms, one or two, or one, two or three, nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl; 1,2,4-triazin-5-yl, 1,2,4-triazin-6-yl and 1,3,5-triazin-2-yl.

"Substituents" for radicals specified herein are especially selected from keto groups, —COOH, —COO-alkyl, —OH, —SH, —CN, amino, —$NO_2$, alkyl, or alkenyl groups.

A3) Polycarboxylic Anhydride Compounds, Such as Especially Polycarboxylic Anhydrides and Hydrocarbyl-Substituted Polycarboxylic Anhydrides The anhydride used is derived from any aliphatic di- or polybasic carboxylic acids (for example tri- or tetrabasic), especially from di-, tri- or tetracarboxylic acids, and is optionally substituted by one or more (for example 2 or 3), especially a long-chain alkyl radical and/or a high molecular weight hydrocarbyl radical, especially a polyalkylene radical. Examples are anhydrides of $C_3$-$C_{10}$ polycarboxylic acids, such as the dicarboxylic acids malonic acid, succinic acid, glutaric acid, adipic acid, pimelic acid, suberic acid, azelaic acid and sebacic acid, and the branched analogs thereof; and the tricarboxylic acid citric acid. The anhydrides can also be obtained from the corresponding monounsaturated acids and addition of at least one long-chain alkyl radical and/or high molecular weight hydrocarbyl radical. Examples of suitable monounsaturated acids are fumaric acid, maleic acid, itaconic acid.

The hydrophobic "long-chain" or "high molecular weight" hydrocarbyl radical which ensures sufficient solubility of the quaternized product in the fuel has a number-average molecular weight ($M_n$) of 85 to 20 000, for example 113 to 10 000, or 200 to 10 000 or 350 to 5000, for example 350 to 3000, 500 to 2500, 700 to 2500, or 800 to 1500. Typical hydrophobic hydrocarbyl radicals include polypropenyl, polybutenyl and polyisobutenyl radicals, for example with a number-average molecular weight $M_n$ of 3500 to 5000, 350 to 3000, 500 to 2500, 700 to 2500 and 800 to 1500.

Suitable hydrocarbyl-substituted anhydrides are described, for example, in DE 43 19 672 and WO 2008/138836.

Suitable hydrocarbyl-substituted polycarboxylic anhydrides also comprise polymeric, especially dimeric, forms of such hydrocarbyl-substituted polycarboxylic anhydrides.

Dimeric forms comprise especially two acid anhydride groups which can be reacted independently with the quaternizable nitrogen compound in the preparation process according to the invention.

A4) Quaternizing Agents

Useful quaternizing agents are in principle all compounds suitable as such. In a particular embodiment, however, the at least one quaternizable tertiary nitrogen atom is quaternized with at least one quaternizing agent selected from epoxides, especially hydrocarbyl epoxides:

(II)

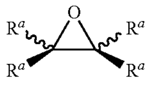

in which the $R^a$ radicals present therein are the same or different and are each H or a hydrocarbyl radical, where the hydrocarbyl radical has at least 1 to 10 carbon atoms. In particular, these are aliphatic or aromatic radicals, for example linear or branched $C_{1-10}$-alkyl radicals, or aromatic radicals, such as phenyl or $C_{1-4}$-alkylphenyl.

Suitable hydrocarbyl epoxides are, for example, aliphatic and aromatic alkylene oxides, such as especially $C_{2-12}$-alkylene oxides, such as ethylene oxide, propylene oxide, 1,2-butylene oxide, 2,3-butylene oxide, 2-methyl-1,2-propene oxide (isobutene oxide), 1,2-pentene oxide, 2,3-pentene oxide, 2-methyl-1,2-butene oxide, 3-methyl-1,2-butene oxide, 1,2-hexene oxide, 2,3-hexene oxide, 3,4-hexene oxide, 2-methyl-1,2-pentene oxide, 2-ethyl-1,2-butene oxide, 3-methyl-1,2-pentene oxide, 1,2-decene oxide, 1,2-dodecene oxide or 4-methyl-1,2-pentene oxide; and also aromatic-substituted ethylene oxides, such as optionally substituted styrene oxide, especially styrene oxide or 4-methylstyrene oxide.

In the case of use of epoxides as quaternizing agents, they are used especially in the absence of free acids, especially in the absence of free protic acids, such as in particular $C_{1-12}$-monocarboxylic acids such as formic acid, acetic acid or propionic acid, or $C_{2-12}$-dicarboxylic acids such as oxalic acid or adipic acid; or else in the absence of sulfonic acids such as benzenesulfonic acid or toluenesulfonic acid, or aqueous mineral acids such as sulfuric acid or hydrochloric acid. The quaternization product thus prepared is thus "acid-free" in the context of the present invention.

A5) Quaternized or Quaternizable Nitrogen Compounds

The quaternizable nitrogen compound reactive with the anhydride is selected from a. hydroxyalkyl-substituted mono- or polyamines having at least one quaternized (e.g. choline) or quaternizable primary, secondary or tertiary amino group;
b. straight-chain or branched, cyclic, heterocyclic, aromatic or nonaromatic polyamines having at least one primary or secondary (anhydride-reactive) amino group and having at least one quaternized or quaternizable primary, secondary or tertiary amino group;
c. piperazines.

The quaternizable nitrogen compound is especially selected from a. hydroxyalkyl-substituted primary, secondary, tertiary or quaternary monoamines and hydroxyalkyl-substituted primary, secondary, tertiary or quaternary diamines;
b. straight-chain or branched aliphatic diamines having two primary amino groups; di- or polyamines having at least one primary and at least one secondary amino group; di- or polyamines having at least one primary and at least one tertiary amino group; di- or polyamines having at least one primary and at least one quaternary amino group; aromatic carbocyclic diamines having two primary amino groups; aromatic heterocyclic polyamines having two primary amino groups; aromatic or nonaromatic heterocycles having one primary and one tertiary amino group.

Examples of suitable "hydroxyalkyl-substituted mono- or polyamines" are those provided with at least one hydroxyalkyl substituents, for example 1, 2, 3, 4, 5 or 6 hydroxyalkyl substituted.

Examples of "hydroxyalkyl-substituted monoamines" include: N-hydroxyalkyl monoamines, N,N-dihydroxyalkyl monoamines and N,N,N-trihydroxyalkyl monoamines, where the hydroxyalkyl groups are the same or different and are also as defined above. Hydroxyalkyl is especially 2-hydroxyethyl, 3-hydroxypropyl or 4-hydroxybutyl.

For example, the following "hydroxyalkyl-substituted polyamines" and especially "hydroxyalkyl-substituted diamines" may be mentioned: (N-hydroxyalkyl)alkylenediamines, N,N-dihydroxyalkylalkylenediamines, where the hydroxyalkyl groups are the same or different and are also as defined above. Hydroxyalkyl is especially 2-hydroxyethyl, 3-hydroxypropyl or 4-hydroxybutyl; alkylene is especially ethylene, propylene or butylene.

Suitable "diamines" are alkylenediamines, and the N-alkyl-substituted analogs thereof, such as N-monoalkylated alkylenediamines and the N,N- or N,N'-dialkylated alkylenediamines. Alkylene is especially straight-chain or branched $C_{1-7}$- or $C_{1-4}$-alkylene as defined above. Alkyl is especially $C_{1-4}$-alkyl as defined above. Examples are in particular ethylenediamine, 1,2-propylenediamine, 1,3-propylenediamine, 1,4-butylenediamine and isomers thereof, pentanediamine and isomers thereof, hexanediamine and isomers thereof, heptanediamine and isomers thereof, as well as singly or multiply, like one- or two-fold $C_1$-$C_4$-alkylated, as for example methylated, derivates of said diamine compounds, as for example 3-dimethylamino-1-propylamine (DMAPA), N,N-diethylaminopropylamine, and N,N-dimethylaminoethylamine.

Suitable straight-chain “polyamines” are, for example, dialkylenetriamine, trialkylenetetramine, tetraalkylenepentamine, pentaalkylenehexamine, and the N-alkyl-substituted analogs thereof, such as N-monoalkylated and the N,N- or N,N'-dialkylated alkylenepolyamines. Alkylene is especially straight-chain or branched $C_{1-7}$- or $C_{1-4}$-alkylene as defined above. Alkyl is especially $C_{1-4}$-alkyl as defined above.

Examples are especially diethylenetriamine, triethylenetetramine, tetraethylenepentamine, pentaethylenehexamine, dipropylenetriamine, tripropylenetetramine, tetrapropylenepentamine, pentapropylenehexamine, dibutylenetriamine, tributylenetetramine, tetrabutylenepentamine, pentabutylenehexamine; and the N,N-dialkyl derivatives thereof, especially the N,N-di-$C_{1-4}$-alkyl derivatives thereof. Examples include: N,N-dimethyldimethylenetriamine, N,N-diethyldimethylenetriamine, N,N-dipropyldimethylenetriamine, N,N-dimethyldiethylene-1,2-triamine, N,N-diethyldiethylene-1,2-triamine, N,N-dipropyldiethylene-1,2-triamine, N,N-dimethyldipropylene-1,3-triamine (i.e. DMAPAPA), N,N-diethyldipropylene-1,3-triamine, N,N-dipropyldipropylene-1,3-triamine, N,N-dimethyldibutylene-1,4-triamine, N,N-diethyldibutylene-1,4-triamine, N,N-dipropyldibutylene-1,4-triamine, N,N-dimethyldipentylene-1,5-triamine, N,N-diethyldipentylene-1,5-triamine, N,N-dipropyldipentylene-1,5-triamine, N,N-dimethyldihexylene-1,6-triamine, N,N-diethyldihexylene-1,6-triamine and N,N-dipropyldihexylene-1,6-triamine.

“Aromatic carbocyclic diamines” having two primary amino groups are the diamino-substituted derivatives of benzene, biphenyl, naphthalene, tetrahydronaphthalene, fluorene, indene and phenanthrene.

“Aromatic or nonaromatic heterocyclic polyamines” having two primary amino groups are the derivatives, substituted by two amino groups, of the following heterocycles:

- 5- or 6-membered, saturated or monounsaturated heterocycles comprising one to two nitrogen atoms and/or one oxygen or sulfur atom or one or two oxygen and/or sulfur atoms as ring members, for example tetrahydrofuran, pyrrolidine, isoxazolidine, isothiazolidine, pyrazolidine, oxazolidine, thiazolidine, imidazolidine, pyrroline, piperidine, piperidinyl, 1,3-dioxane, tetrahydropyran, hexahydropyridazine, hexahydropyrimidine, piperazine;
- 5-membered aromatic heterocycles comprising, in addition to carbon atoms, two or three nitrogen atoms or one or two nitrogen atoms and one sulfur or oxygen atom as ring members, for example furan, thiane, pyrrole, pyrazole, oxazole, thiazole, imidazole and 1,3,4-triazole; isoxazole, isothiazole, thiadiazole, oxadiazole;
- 6-membered heterocycles comprising, in addition to carbon atoms, one or two, or one, two or three, nitrogen atoms as ring members, for example pyridinyl, pyridazine, pyrimidine, pyrazinyl, 1,2,4-triazine, 1,3,5-triazin-2-yl.

“Aromatic or nonaromatic heterocycles having one primary and one tertiary amino group” are, for example, the abovementioned N-heterocycles which are aminoalkylated on at least one ring nitrogen atom, and especially bear an amino-$C_{1-4}$-alkyl group.

“Aromatic or nonaromatic heterocycles having a tertiary amino group and a hydroxyalkyl group” are, for example, the abovementioned N-heterocycles which are hydroxyalkylated on at least one ring nitrogen atom, and especially bear a hydroxy-$C_{1-4}$-alkyl group.

Mention should be made especially of the following groups of individual classes of quaternizable nitrogen compounds:

Group 1:

| NAME | FORMULA |
|---|---|
| Diamines with primary second nitrogen atom | |
| Ethylenediamine | 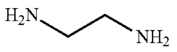 |
| 1,2-Propylenediamine | 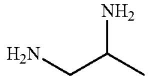 |
| 1,3-Propylenediamine | 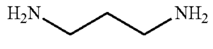 |
| Isomeric butylenediamines, for example | 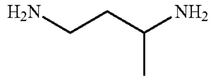 |
| 1,5-Pentylenediamine | 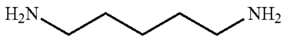 |
| Isomeric pentanediamines, for example | 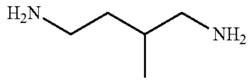 |
| Isomeric hexanediamines, for example | 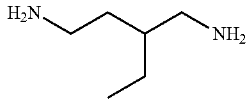 |
| Isomeric heptanediamines, for example | 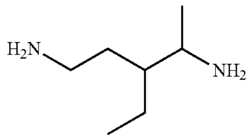 |
| Di- and polyamines with a secondary second nitrogen atom | |
| Diethylenetriamine (DETA) | 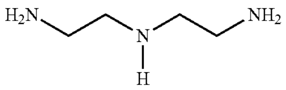 |
| Dipropylenetriamine (DPTA), 3,3'-iminobis(N,N-dimethylpropylamine) | 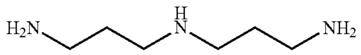 |
| Triethylenetetramine (TETA) | 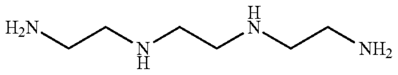 |
| Tetraethylenepentamine (TEPA) | 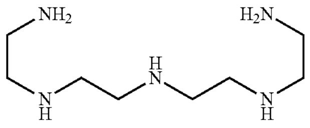 [SMILES: NCCNCCNCCNCCN] |
| Pentaethylenehexamine | 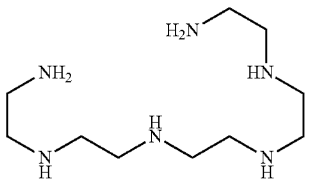 [SMILES: NCCNCCNCCNCCNCCN] |

-continued

| NAME | FORMULA |
|---|---|
| N-Methyl-3-amino-1-propylamine | 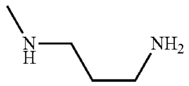 |
| Bishexamethylene-triamine | 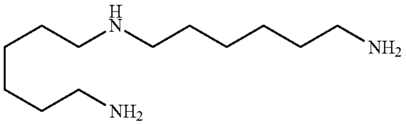 [SMILES: NCCCCCCNCCCCCCN] |
| Aromatics | |
| Diaminobenzenes, for example | 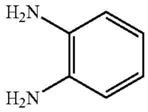 |
| Diaminopyridines, for example | 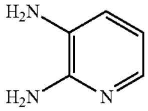 |

Group 2:

| NAME | FORMULA |
|---|---|
| Heterocycles | |
| 1-(3-Aminopropyl)imidazole | 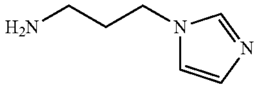 |
| 4-(3-Aminopropyl)morpholine | 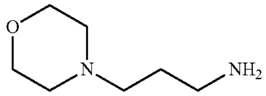 |
| 1-(2-Aminoethylpiperidine) | 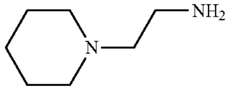 |
| 2-(1-Piperazinyl)ethylamine (AEP) | 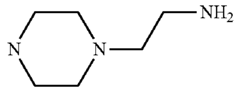 |
| N-Methylpiperazine | 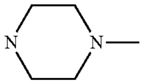 |
| Amines with a tertiary second nitrogen atom | |
| 3,3-Diamino-N-methyldipropylamine | 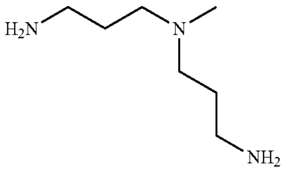 |
| 3-Dimethylamino-1-propylamine (DMAPA) | 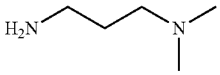 |

-continued

| NAME | FORMULA |
|---|---|
| N,N-Diethylaminopropylamine | 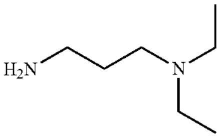 |
| N,N-Dimethylaminoethylamine | 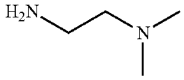 |

Group 3:

| NAME | FORMULA |
|---|---|
| Alcohols with a primary and secondary amine | |
| Ethanolamine | 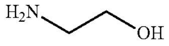 |
| 3-Hydroxy-1-propylamine | 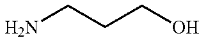 |
| Diethanolamine | 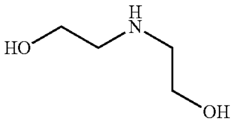 |
| Diisopropanolamine | 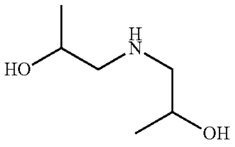 |
| N-(2-Hydroxyethyl)ethylenediamine | 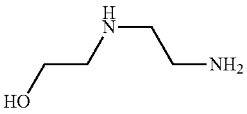 |
| Alcohols with a tertiary amine | |
| Triethanolamine, (2,2',2''-Nitrilotriethanol) | 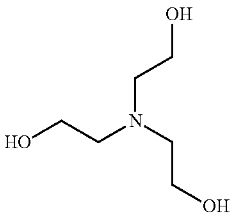 |
| 1-(3-Hydroxypropyl)imidazole | 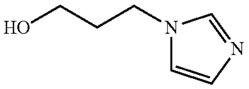 |
| Tris(hydroxymethyl)amine | 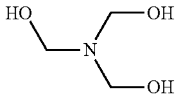 |
| 3-Dimethylamino-1-propanol | 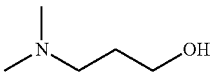 |

-continued

| NAME | FORMULA |
| --- | --- |
| 3-Diethylamino-1-propanol | 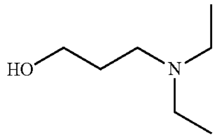 |
| 2-Dimethylamino-1-ethanol | 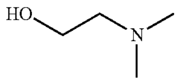 |
| 4-Diethylamino-1-butanol | 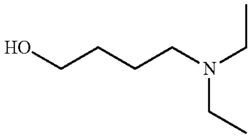 |

A6) Preparation of Inventive Additives a) Amine Addition and Alcohol Addition

The hydrocarbyl-substituted polycarboxylic anhydride compound is reacted with the quaternizable nitrogen compound under thermally controlled conditions, such that there is essentially no condensation reaction. More particularly, in accordance with the invention, no formation of water of reaction is observed. More particularly, the reaction is effected at a temperature in the range from 10 to 80° C., especially 20 to 60° C. or 30 to 50° C. The reaction time may be in the range from a few minutes or a few hours, for example about 1 minute up to about 10 hours. The reaction can be effected at a pressure of about 0.1 to 2 atm, but especially at approximately standard pressure. In particular, an inert gas atmosphere, for example nitrogen, is appropriate.

The reactants are initially charged especially in about equimolar amounts; optionally, a small molar excess of the anhydride, for example a 0.05- to 0.5-fold, for example a 0.1- to 0.3-fold, excess, is desirable. If required, the reactants can be initially charged in a suitable inert organic aliphatic or aromatic solvent or a mixture thereof. Typical examples are, for example, solvents of the Solvesso series, toluene or xylene. However, in another particular embodiment, the reaction is effected in the absence of organic solvents, especially protic solvents.

In the case of inventive performance of the reaction, the anhydride ring is opened with addition of the quaternizable nitrogen compound via the reactive oxygen or nitrogen group thereof (for example hydroxyl group or primary or secondary amine group), and without the elimination of water of condensation. The reaction product obtained comprises a polycarboxylic intermediate with at least one newly formed acid amide group or ester group and at least one intramolecular, bound, newly formed carboxylic acid or carboxylate group, in a stoichiometric proportion relative to the quaternizable amino group bound intramolecularly by the addition reaction.

The reaction product thus formed can theoretically be purified further, or the solvent can be removed. Usually, however, this is not absolutely necessary, such that the reaction step can be transferred without further purification into the next synthesis step, the quaternization.

b) Quaternization

The epoxide-based quaternization in reaction step (b) is then carried out without addition of acid, in a complete renunciation of prior art methods described to date. The carboxyl radical formed by amine addition promotes the epoxide ring opening and hence the quaternization of the amino group. The reaction product obtained therefore does not have a free acid anion. Nevertheless, the product is uncharged owing to its betaine structure.

To perform the quaternization, the reaction product or reaction mixture from stage a) is admixed with at least one epoxide compound of the above formula (II), especially in the stoichiometric amounts required to achieve the desired quaternization. It is possible to use, for example, 0.1 to 1.5 equivalents, or 0.5 to 1.25 equivalents, of quaternizing agent per equivalent of quaternizable tertiary nitrogen atom. More particularly, however, approximately equimolar proportions of the epoxide are used to quaternize a tertiary amine group. Correspondingly higher use amounts are required to quaternize a secondary or primary amine group.

Typical working temperatures here are in the range from 15 to 90° C., especially from 20 to 80° C. or 30 to 70° C. The reaction time may be in the range of a few minutes or a few hours, for example about 10 minutes up to about 24 hours. The reaction can be effected at a pressure of about 0.1 to 20 bar, for example 1 to 10 or 1.5 to 3 bar, but especially at about standard pressure. More particularly, an inert gas atmosphere, for example nitrogen, is appropriate.

If required, the reactants can be initially charged for the epoxidation in a suitable inert organic aliphatic or aromatic solvent or a mixture thereof, or a sufficient proportion of solvent from reaction step a) is still present. Typical examples are, for example, solvents of the Solvesso series, toluene or xylene. In a further particular embodiment, the reaction, however, is performed in the absence of organic solvents, especially protic (organic) solvents.

"Protic solvents", which are especially not used in accordance with the invention, are especially those with a dielectric constant of greater than 9. Such protic solvents usually comprise at least one HO group and may additionally contain water. Typical examples are, for example, glycols and glycol ethers, and alcohols such as aliphatic, cyclic-aliphatic, aromatic or heterocyclic alcohols.

c) Workup of the Reaction Mixture

The reaction end product thus formed can theoretically be purified further, or the solvent can be removed. Usually, however, this is not absolutely necessary, and so the reaction product is usable without further purification as an additive, optionally after blending with further additive components (see below), especially since there are of course also no corrosive free protic acids present in the reaction product.

d) General Example

As a nonlimiting example of the reaction of a polyalkylene-substituted dicarboxylic anhydride compound by amine addition or alcohol addition and subsequent quaternization, reference is made to the following illustrative reaction schemes in which $R_1$ to $R_7$, $L_1$ and $L_2$ are each as defined above:

Stage 1: Preparation of the Substituted Dicarboxylic Anhydride
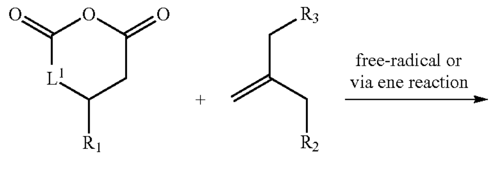
1-2 mol. eq.
1 mol. eq.
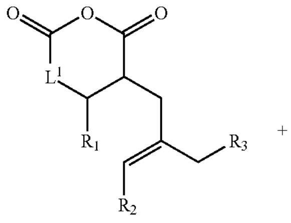
(A)
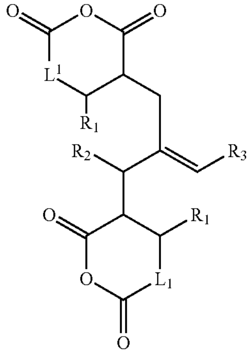
(B)
Stage 2a: Amination and Quaternization
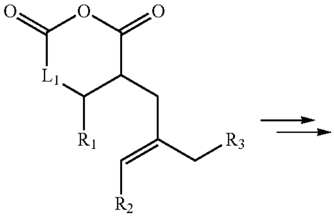
(A)
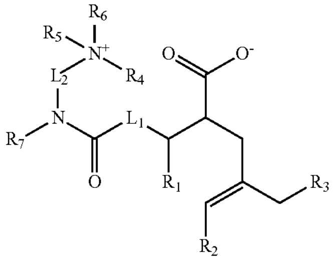
(Ia-1)
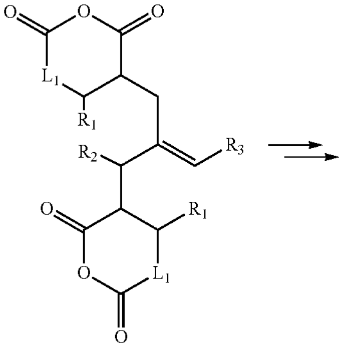
(B)
-continued
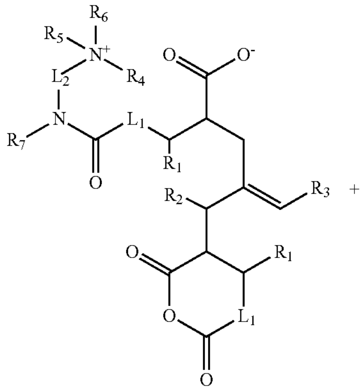
(Ia-2)
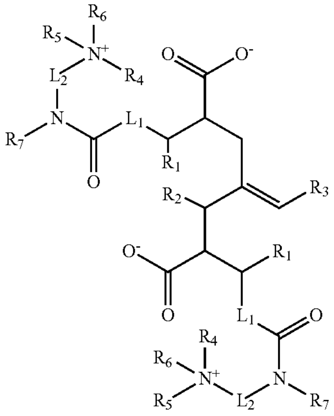
(Ia-3)
Stage 2b: Ester Formation and Quaternization
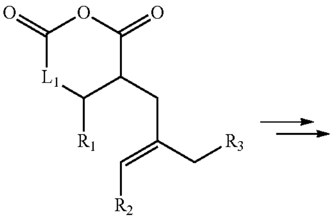
(A)
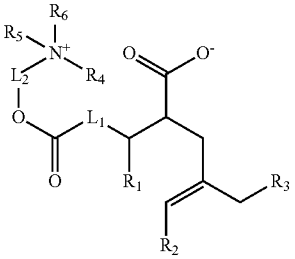
(Ib-1)

-continued

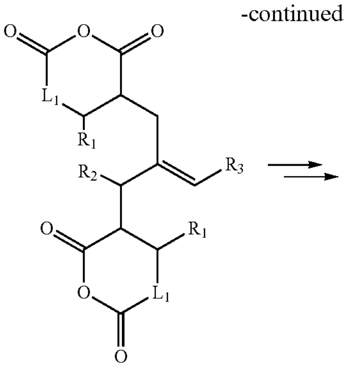

(B)

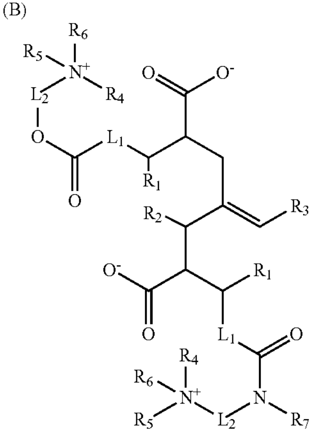

+

(Ib-3)

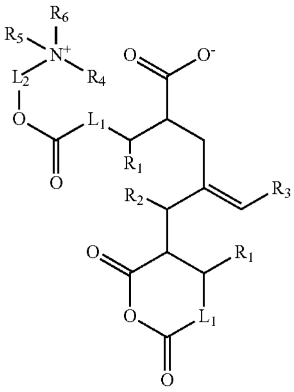

(Ib-2)

B) Further Additive Components

The fuel additized with the inventive quaternized additive is a gasoline fuel or especially a middle distillate fuel, in particular a diesel fuel.

The fuel may comprise further customary additives to improve efficacy and/or suppress wear.

In the case of diesel fuels, these are primarily customary detergent additives, carrier oils, cold flow improvers, lubricity improvers, corrosion inhibitors, demulsifiers, dehazers, antifoams, cetane number improvers, combustion improvers, antioxidants or stabilizers, antistats, metallocenes, metal deactivators, dyes and/or solvents.

In the case of gasoline fuels, these are in particular lubricity improvers (friction modifiers), corrosion inhibitors, demulsifiers, dehazers, antifoams, combustion improvers, antioxidants or stabilizers, antistats, metallocenes, metal deactivators, dyes and/or solvents.

Typical examples of suitable coadditives are listed in the following section:

B1) Detergent Additives

The customary detergent additives are preferably amphiphilic substances which possess at least one hydrophobic hydrocarbon radical with a number-average molecular weight ($M_e$) of 85 to 20 000 and at least one polar moiety selected from:

(Da) mono- or polyamino groups having up to 6 nitrogen atoms, at least one nitrogen atom having basic properties;

(Db) nitro groups, optionally in combination with hydroxyl groups;

(Dc) hydroxyl groups in combination with mono- or polyamino groups, at least one nitrogen atom having basic properties;

(Dd) carboxyl groups or their alkali metal or alkaline earth metal salts;

(De) sulfonic acid groups or their alkali metal or alkaline earth metal salts;

(Df) polyoxy-$C_2$- to $C_4$-alkylene moieties terminated by hydroxyl groups, mono- or polyamino groups, at least one nitrogen atom having basic properties, or by carbamate groups;

(Dg) carboxylic ester groups;

(Dh) moieties derived from succinic anhydride and having hydroxyl and/or amino and/or amido and/or imido groups; and/or (Di) moieties obtained by Mannich reaction of substituted phenols with aldehydes and mono- or polyamines.

The hydrophobic hydrocarbon radical in the above detergent additives, which ensures the adequate solubility in the fuel, has a number-average molecular weight ($M_e$) of 85 to 20 000, preferably of 113 to 10 000, more preferably of 300 to 5000, even more preferably of 300 to 3000, even more especially preferably of 500 to 2500 and especially of 700 to 2500, in particular of 800 to 1500. As typical hydrophobic hydrocarbon radicals, especially in conjunction with the polar groups especially polypropenyl, polybutenyl and polyisobutenyl radicals with a number-average molecular weight $M_n$ of preferably in each case 300 to 5000, more preferably 300 to 3000, even more preferably 500 to 2500, even more especially preferably 700 to 2500 and especially 800 to 1500 are taken into consideration.

Examples of the above groups of detergent additives include the following:

Additives comprising mono- or polyamino groups (Da) are preferably polyalkenemono- or polyalkenepolyamines based on polypropene or on high-reactivity (i.e. having predominantly terminal double bonds) or conventional (i.e. having predominantly internal double bonds) polybutene or polyisobutene having $M_n$=300 to 5000, more preferably 500 to 2500 and especially 700 to 2500. Such additives based on high-reactivity polyisobutene, which can be prepared from the polyisobutene which may comprise up to 20% by weight of n-butene units by hydroformylation and reductive amination with ammonia, monoamines or polyamines such as dimethylaminopropylamine, ethylenediamine, diethylenetriamine, triethylenetetramine or tetraethylenepentamine, are known especially from EP-A 244 616. When polybutene or polyisobutene having predominantly internal double bonds (usually in the β and γ positions) are used as starting materials in the preparation of the additives, a possible preparative route is by chlorination and subsequent amination or by oxidation of the double bond with air or ozone to give the carbonyl or carboxyl compound and subsequent amination under reductive (hydrogenating) conditions. The amines used here for the amination may be, for example, ammonia, monoamines or the abovementioned polyamines. Corresponding additives based on polypropene are described in particular in WO-A 94/24231.

Further particular additives comprising monoamino groups (Da) are the hydrogenation products of the reaction products of polyisobutenes having an average degree of polymerization P=5 to 100 with nitrogen oxides or mixtures of nitrogen oxides and oxygen, as described in particular in WO-A 97/03946.

Further particular additives comprising monoamino groups (Da) are the compounds obtainable from polyisobutene epoxides by reaction with amines and subsequent dehydration and reduction of the amino alcohols, as described in particular in DE-A 196 20 262.

Additives comprising nitro groups (Db), optionally in combination with hydroxyl groups, are preferably reaction products of polyisobutenes having an average degree of polymerization P=5 to 100 or 10 to 100 with nitrogen oxides or mixtures of nitrogen oxides and oxygen, as described in particular in WO-A 96/03367 and in WO-A 96/03479. These reaction products are generally mixtures of pure nitropolyisobutenes (e.g. $\alpha,\beta$-dinitropolyisobutene) and mixed hydroxynitropolyisobutenes (e.g. $\alpha$-nitro-$\beta$-hydroxypolyisobutene).

Additives comprising hydroxyl groups in combination with mono- or polyamino groups (Dc) are in particular reaction products of polyisobutene epoxides obtainable from polyisobutene having preferably predominantly terminal double bonds and $M_n$=300 to 5000, with ammonia or mono- or polyamines, as described in particular in EP-A 476 485.

Additives comprising carboxyl groups or their alkali metal or alkaline earth metal salts (Dd) are preferably copolymers of $C_2$- to $C_{40}$-olefins with maleic anhydride which have a total molar mass of 500 to 20 000 and some or all of whose carboxyl groups have been converted to the alkali metal or alkaline earth metal salts and any remainder of the carboxyl groups has been reacted with alcohols or amines. Such additives are disclosed in particular by EP-A 307 815. Such additives serve mainly to prevent valve seat wear and can, as described in WO-A 87/01126, advantageously be used in combination with customary fuel detergents such as poly(iso)buteneamines or polyetheramines.

Additives comprising sulfonic acid groups or their alkali metal or alkaline earth metal salts (De) are preferably alkali metal or alkaline earth metal salts of an alkyl sulfosuccinate, as described in particular in EP-A 639 632. Such additives serve mainly to prevent valve seat wear and can be used advantageously in combination with customary fuel detergents such as poly(iso)buteneamines or polyetheramines.

Additives comprising polyoxy-$C_2$-$C_4$-alkylene moieties (Df) are preferably polyethers or polyetheramines which are obtainable by reaction of $C_2$- to $C_{60}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with 1 to 30 mol of ethylene oxide and/or propylene oxide and/or butylene oxide per hydroxyl group or amino group and, in the case of the polyetheramines, by subsequent reductive amination with ammonia, monoamines or polyamines. Such products are described in particular in EP-A 310 875, EP-A 356 725, EP-A 700 985 and US-A 4 877 416. In the case of polyethers, such products also have carrier oil properties. Typical examples of these are tridecanol butoxylates, isotridecanol butoxylates, isononylphenol butoxylates and polyisobutenol butoxylates and propoxylates and also the corresponding reaction products with ammonia.

Additives comprising carboxylic ester groups (Dg) are preferably esters of mono-, di- or tricarboxylic acids with long-chain alkanols or polyols, in particular those having a minimum viscosity of 2 $mm^2/s$ at 100° C., as described in particular in DE-A 38 38 918. The mono-, di- or tricarboxylic acids used may be aliphatic or aromatic acids, and particularly suitable ester alcohols or ester polyols are long-chain representatives having, for example, 6 to 24 carbon atoms. Typical representatives of the esters are adipates, phthalates, isophthalates, terephthalates and trimellitates of isooctanol, of isononanol, of isodecanol and of isotridecanol. Such products also have carrier oil properties.

Additives comprising moieties derived from succinic anhydride and having hydroxyl and/or amino and/or amido and/or especially imido groups (Dh) are preferably corresponding derivatives of alkyl- or alkenyl-substituted succinic anhydride and especially the corresponding derivatives of polyisobutenylsuccinic anhydride which are obtainable by reacting conventional or high-reactivity polyisobutene having $M_n$=preferably 300 to 5000, more preferably 300 to 3000, even more preferably 500 to 2500, even more especially preferably 700 to 2500 and especially 800 to 1500, with maleic anhydride by a thermal route in an ene reaction or via the chlorinated polyisobutene. The moieties having hydroxyl and/or amino and/or amido and/or imido groups are, for example, carboxylic acid groups, acid amides of monoamines, acid amides of di- or polyamines which, in addition to the amide function, also have free amine groups, succinic acid derivatives having an acid and an amide function, carboximides with monoamines, carboximides with di- or polyamines which, in addition to the imide function, also have free amine groups, or diimides which are formed by the reaction of di- or polyamines with two succinic acid derivatives. In the presence of imido moieties D(h), the further detergent additive in the context of the present invention is, however, used only up to a maximum of 100% of the weight of compounds with betaine structure. Such fuel additives are common knowledge and are described, for example, in documents (1) and (2). They are preferably the reaction products of alkyl- or alkenyl-substituted succinic acids or derivatives thereof with amines and more preferably the reaction products of polyisobutenyl-substituted succinic acids or derivatives thereof with amines. Of particular interest in this context are reaction products with aliphatic polyamines (polyalkyleneimines) such as especially ethylenediamine, diethylenetriamine, triethylenetetramine, tetraethylenepentamine, pentaethylenehexamine and hexaethyleneheptamine, which have an imide structure.

Additives comprising moieties (Di) obtained by Mannich reaction of substituted phenols with aldehydes and mono- or polyamines are preferably reaction products of polyisobutene-substituted phenols with formaldehyde and mono- or polyamines such as ethylenediamine, diethylenetriamine, triethylenetetramine, tetraethylenepentamine or dimethylaminopropylamine. The polyisobutenyl-substituted phenols may stem from conventional or high-reactivity polyisobutene having $M_n$=300 to 5000. Such "polyisobutene Mannich bases" are described in particular in EP-A 831 141.

One or more of the detergent additives mentioned can be added to the fuel in such an amount that the dosage of these detergent additives is preferably 25 to 2500 ppm by weight, especially 75 to 1500 ppm by weight, in particular 150 to 1000 ppm by weight.

B2) Carrier Oils

Carrier oils additionally used may be of mineral or synthetic nature. Suitable mineral carrier oils are the fractions obtained in crude oil processing, such as brightstock or base oils having viscosities, for example, from the SN 500 to 2000 class; but also aromatic hydrocarbons, paraffinic hydrocarbons and alkoxyalkanols. Likewise useful is a fraction which is obtained in the refining of mineral oil and is known as "hydrocrack oil" (vacuum distillate cut having a boiling range from about 360 to 500° C., obtainable from natural mineral oil which has been catalytically hydrogenated and isomerized under high pressure and also deparaffinized). Likewise suitable are mixtures of the abovementioned mineral carrier oils.

Examples of suitable synthetic carrier oils are polyolefins (polyalphaolefins or polyinternalolefins), (poly)esters, (poly) alkoxylates, polyethers, aliphatic polyetheramines, alkylphenol-started polyethers, alkylphenol-started polyetheramines and carboxylic esters of long-chain alkanols.

Examples of suitable polyolefins are olefin polymers having $M_n$=400 to 1800, in particular based on polybutene or polyisobutene (hydrogenated or unhydrogenated).

Examples of suitable polyethers or polyetheramines are preferably compounds comprising polyoxy-$C_2$- to $C_4$-alkylene moieties which are obtainable by reacting $C_2$- to $C_{60}$-alkanols, $C_6$- to $C_{30}$-alkanediols, mono- or di-$C_2$- to $C_{30}$-alkylamines, $C_1$- to $C_{30}$-alkylcyclohexanols or $C_1$- to $C_{30}$-alkylphenols with 1 to 30 mol of ethylene oxide and/or propylene oxide and/or butylene oxide per hydroxyl group or amino group, and, in the case of the polyetheramines, by subsequent reductive amination with ammonia, monoamines or polyamines. Such products are described in particular in EP-A 310 875, EP-A 356 725, EP-A 700 985 and U.S. Pat. No. 4,877,416. For example, the polyetheramines used may be poly-$C_2$- to $C_6$-alkylene oxide amines or functional derivatives thereof. Typical examples thereof are tridecanol butoxylates or isotridecanol butoxylates, isononylphenol butoxylates and also polyisobutenol butoxylates and propoxylates, and also the corresponding reaction products with ammonia.

Examples of carboxylic esters of long-chain alkanols are in particular esters of mono-, di- or tricarboxylic acids with long-chain alkanols or polyols, as described in particular in DE-A 38 38 918. The mono-, di- or tricarboxylic acids used may be aliphatic or aromatic acids; suitable ester alcohols or polyols are in particular long-chain representatives having, for example, 6 to 24 carbon atoms. Typical representatives of the esters are adipates, phthalates, isophthalates, terephthalates and trimellitates of isooctanol, isononanol, isodecanol and isotridecanol, for example di(n- or isotridecyl) phthalate.

Further suitable carrier oil systems are described, for example, in DE-A 38 26 608, DE-A 41 42 241, DE-A 43 09 074, EP-A 452 328 and EP-A 548 617.

Examples of particularly suitable synthetic carrier oils are alcohol-started polyethers having about 5 to 35, preferably about 5 to 30, more preferably 10 to 30 and especially 15 to 30 $C_3$- to $C_6$-alkylene oxide units, for example selected from propylene oxide, n-butylene oxide and isobutylene oxide units, or mixtures thereof, per alcohol molecule. Nonlimiting examples of suitable starter alcohols are long-chain alkanols or phenols substituted by long-chain alkyl in which the long-chain alkyl radical is in particular a straight-chain or branched $C_6$- to $C_{18}$-alkyl radical. Particular examples include tridecanol and nonylphenol. Particularly preferred alcohol-started polyethers are the reaction products (polyetherification products) of monohydric aliphatic $C_6$- to $C_{18}$-alcohols with $C_3$- to $C_6$-alkylene oxides. Examples of monohydric aliphatic $C_6$-$C_{18}$-alcohols are hexanol, heptanol, octanol, 2-ethylhexanol, nonyl alcohol, decanol, 3-propylheptanol, undecanol, dodecanol, tridecanol, tetradecanol, pentadecanol, hexadecanol, octadecanol and the constitutional and positional isomers thereof. The alcohols can be used either in the form of the pure isomers or in the form of technical grade mixtures. A particularly preferred alcohol is tridecanol. Examples of $C_3$- to $C_6$-alkylene oxides are propylene oxide, such as 1,2-propylene oxide, butylene oxide, such as 1,2-butylene oxide, 2,3-butylene oxide, isobutylene oxide or tetrahydrofuran, pentylene oxide and hexylene oxide. Particular preference among these is given to $C_3$- to $C_4$-alkylene oxides, i.e. propylene oxide such as 1,2-propylene oxide and butylene oxide such as 1,2-butylene oxide, 2,3-butylene oxide and isobutylene oxide. Especially butylene oxide is used.

Further suitable synthetic carrier oils are alkoxylated alkylphenols, as described in DE-A 10 102 913.

Particular carrier oils are synthetic carrier oils, particular preference being given to the above-described alcohol-started polyethers.

The carrier oil or the mixture of different carrier oils is added to the fuel in an amount of preferably 1 to 1000 ppm by weight, more preferably of 10 to 500 ppm by weight and especially of 20 to 100 ppm by weight.

B3) Cold Flow Improvers

Suitable cold flow improvers are in principle all organic compounds which are capable of improving the flow performance of middle distillate fuels or diesel fuels under cold conditions. For the intended purpose, they must have sufficient oil solubility. In particular, useful cold flow improvers for this purpose are the cold flow improvers (middle distillate flow improvers, MDFIs) typically used in the case of middle distillates of fossil origin, i.e. in the case of customary mineral diesel fuels. However, it is also possible to use organic compounds which partly or predominantly have the properties of a wax antisettling additive (WASA) when used in customary diesel fuels. They can also act partly or predominantly as nucleators. It is, though, also possible to use mixtures of organic compounds effective as MDFIs and/or effective as WASAs and/or effective as nucleators.

The cold flow improver is typically selected from (K1) copolymers of a $C_2$- to $C_{40}$-olefin with at least one further ethylenically unsaturated monomer;

(K2) comb polymers;

(K3) polyoxyalkylenes;

(K4) polar nitrogen compounds;

(K5) sulfocarboxylic acids or sulfonic acids or derivatives thereof; and (K6) poly(meth)acrylic esters.

It is possible to use either mixtures of different representatives from one of the particular classes (K1) to (K6) or mixtures of representatives from different classes (K1) to (K6).

Suitable $C_2$- to $C_{40}$-olefin monomers for the copolymers of class (K1) are, for example, those having 2 to 20 and especially 2 to 10 carbon atoms, and 1 to 3 and preferably 1 or 2 carbon-carbon double bonds, especially having one carbon-carbon double bond. In the latter case, the carbon-carbon double bond may be arranged either terminally α-olefins) or internally. However, preference is given to α-olefins, more preferably α-olefins having 2 to 6 carbon atoms, for example propene, 1-butene, 1-pentene, 1-hexene and in particular ethylene.

In the copolymers of class (K1), the at least one further ethylenically unsaturated monomer is preferably selected from alkenyl carboxylates, (meth)acrylic esters and further olefins.

When further olefins are also copolymerized, they are preferably higher in molecular weight than the abovementioned $C_2$- to $C_{40}$-olefin base monomer. When, for example, the olefin base monomer used is ethylene or propene, suitable further olefins are in particular $C_{10}$- to $C_{40}$-α-olefins. Further olefins are in most cases only additionally copolymerized when monomers with carboxylic ester functions are also used.

Suitable (meth)acrylic esters are, for example, esters of (meth)acrylic acid with $C_1$- to $C_{20}$-alkanols, especially $C_1$- to $C_{10}$-alkanols, in particular with methanol, ethanol, propanol, isopropanol, n-butanol, sec-butanol, isobutanol, tert-butanol, pentanol, hexanol, heptanol, octanol, 2-ethylhexanol, nonanol and decanol, and structural isomers thereof.

Suitable alkenyl carboxylates are, for example, $C_2$- to $C_{14}$-alkenyl esters, for example the vinyl and propenyl esters, of carboxylic acids having 2 to 21 carbon atoms, whose hydrocarbon radical may be linear or branched. Among these, preference is given to the vinyl esters. Among the carboxylic acids with a branched hydrocarbon radical, preference is given to those whose branch is in the α-position to the carboxyl group, the α-carbon atom more preferably being tertiary, i.e. the carboxylic acid being a so-called neocarboxylic acid. However, the hydrocarbon radical of the carboxylic acid is preferably linear.

Examples of suitable alkenyl carboxylates are vinyl acetate, vinyl propionate, vinyl butyrate, vinyl 2-ethylhexanoate, vinyl neopentanoate, vinyl hexanoate, vinyl neononanoate, vinyl neodecanoate and the corresponding propenyl esters, preference being given to the vinyl esters. A particularly preferred alkenyl carboxylate is vinyl acetate; typical copolymers of group (K1) resulting therefrom are ethylene-vinyl acetate copolymers ("EVAs"), which are some of the most frequently used. Ethylene-vinyl acetate copolymers usable particularly advantageously and their preparation are described in WO 99/29748.

Suitable copolymers of class (K1) are also those which comprise two or more different alkenyl carboxylates in copolymerized form, which differ in the alkenyl function and/or in the carboxylic acid group. Likewise suitable are copolymers which, as well as the alkenyl carboxylate(s), comprise at least one olefin and/or at least one (meth)acrylic ester in copolymerized form.

Terpolymers of a $C_2$- to $C_{40}$-α-olefin, a $C_1$- to $C_{20}$-alkyl ester of an ethylenically unsaturated monocarboxylic acid having 3 to 15 carbon atoms and a $C_2$- to $C_{14}$-alkenyl ester of a saturated monocarboxylic acid having 2 to 21 carbon atoms are also suitable as copolymers of class (K1). Terpolymers of this kind are described in WO 2005/054314. A typical terpolymer of this kind is formed from ethylene, 2-ethylhexyl acrylate and vinyl acetate.

The at least one or the further ethylenically unsaturated monomer(s) are copolymerized in the copolymers of class (K1) in an amount of preferably 1 to 50% by weight, especially 10 to 45% by weight and in particular 20 to 40% by weight, based on the overall copolymer. The main proportion in terms of weight of the monomer units in the copolymers of class (K1) therefore originates generally from the $C_2$ to $C_{40}$ base olefins.

The copolymers of class (K1) preferably have a number-average molecular weight $M_n$ of 1000 to 20 000, more preferably 1000 to 10 000 and in particular 1000 to 8000.

Typical comb polymers of component (K2) are, for example, obtainable by the copolymerization of maleic anhydride or fumaric acid with another ethylenically unsaturated monomer, for example with an α-olefin or an unsaturated ester, such as vinyl acetate, and subsequent esterification of the anhydride or acid function with an alcohol having at least 10 carbon atoms. Further suitable comb polymers are copolymers of α-olefins and esterified comonomers, for example esterified copolymers of styrene and maleic anhydride or esterified copolymers of styrene and fumaric acid. Suitable comb polymers may also be polyfumarates or polymaleates. Homo- and copolymers of vinyl ethers are also suitable comb polymers. Comb polymers suitable as components of class (K2) are, for example, also those described in WO 2004/035715 and in "Comb-Like Polymers. Structure and Properties", N. A. Platé and V. P. Shibaev, J. Poly. Sci. Macromolecular Revs. 8, pages 117 to 253 (1974)". Mixtures of comb polymers are also suitable.

Polyoxyalkylenes suitable as components of class (K3) are, for example, polyoxyalkylene esters, polyoxyalkylene ethers, mixed polyoxyalkylene ester/ethers and mixtures thereof. These polyoxyalkylene compounds preferably comprise at least one linear alkyl group, preferably at least two linear alkyl groups, each having 10 to 30 carbon atoms and a polyoxyalkylene group having a number-average molecular weight of up to 5000. Such polyoxyalkylene compounds are described, for example, in EP-A 061 895 and also in U.S. Pat. No. 4,491,455. Particular polyoxyalkylene compounds are based on polyethylene glycols and polypropylene glycols having a number-average molecular weight of 100 to 5000. Additionally suitable are polyoxyalkylene mono- and diesters of fatty acids having 10 to 30 carbon atoms, such as stearic acid or behenic acid.

Polar nitrogen compounds suitable as components of class (K4) may be either ionic or nonionic and preferably have at least one substituent, in particular at least two substituents, in the form of a tertiary nitrogen atom of the general formula $>NR^7$ in which $R^7$ is a $C_8$- to $C_{40}$-hydrocarbon radical. The nitrogen substituents may also be quaternized, i.e. be in cationic form. An example of such nitrogen compounds is that of ammonium salts and/or amides which are obtainable by the reaction of at least one amine substituted by at least one hydrocarbon radical with a carboxylic acid having 1 to 4 carboxyl groups or with a suitable derivative thereof. The amines preferably comprise at least one linear $C_8$- to $C_{40}$-alkyl radical. Primary amines suitable for preparing the polar nitrogen compounds mentioned are, for example, octylamine, nonylamine, decylamine, undecylamine, dodecylamine, tetradecylamine and the higher linear homologs. Secondary amines suitable for this purpose are, for example, dioctadecylamine and methylbehenylamine. Also suitable for this purpose are amine mixtures, in particular amine mixtures obtainable on the industrial scale, such as fatty amines or hydrogenated tallamines, as described, for example, in Ullmann's Encyclopedia of Industrial Chemistry, 6th Edition, "Amines, aliphatic" chapter. Acids suitable for the reaction are, for example, cyclohexane-1,2-dicarboxylic acid, cyclohexene-1,2-dicarboxylic acid, cyclopentane-1,2-dicarboxylic acid, naphthalenedicarboxylic acid, phthalic acid, isophthalic acid, terephthalic acid, and succinic acids substituted by long-chain hydrocarbon radicals.

In particular, the component of class (K4) is an oil-soluble reaction product of poly($C_2$- to $C_{20}$-carboxylic acids) having at least one tertiary amino group with primary or secondary amines. The poly($C_2$- to $C_{20}$-carboxylic acids) which have at least one tertiary amino group and form the basis of this reaction product comprise preferably at least 3 carboxyl groups, especially 3 to 12 and in particular 3 to 5 carboxyl groups. The carboxylic acid units in the polycarboxylic acids have preferably 2 to 10 carbon atoms, and are especially acetic acid units. The carboxylic acid units are suitably bonded to the polycarboxylic acids, usually via one or more carbon and/or nitrogen atoms. They are preferably attached to tertiary nitrogen atoms which, in the case of a plurality of nitrogen atoms, are bonded via hydrocarbon chains.

The component of class (K4) is preferably an oil-soluble reaction product based on poly($C_2$- to $C_{20}$-carboxylic acids) which have at least one tertiary amino group and are of the general formula IIa or IIb (IIa)

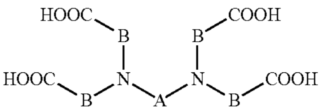

(IIb)

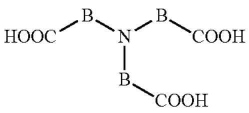

in which the variable A is a straight-chain or branched $C_2$- to $C_6$-alkylene group or the moiety of the formula III (III)

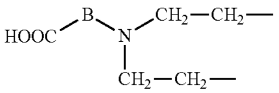

and the variable B is a $C_1$- to $C_{19}$-alkylene group. The compounds of the general formulae IIa and IIb especially have the properties of a WASA.

Moreover, the preferred oil-soluble reaction product of component (K4), especially that of the general formula IIa or IIb, is an amide, an amide-ammonium salt or an ammonium salt in which no, one or more carboxylic acid groups have been converted to amide groups.

Straight-chain or branched $C_2$- to $C_6$-alkylene groups of the variable A are, for example, 1,1-ethylene, 1,2-propylene, 1,3-propylene, 1,2-butylene, 1,3-butylene, 1,4-butylene, 2-methyl-1,3-propylene, 1,5-pentylene, 2-methyl-1,4-butylene, 2,2-dimethyl-1,3-propylene, 1,6-hexylene (hexamethylene) and in particular 1,2-ethylene. The variable A comprises preferably 2 to 4 and especially 2 or 3 carbon atoms.

$C_1$- to $C_{19}$-alkylene groups of the variable B are, for example, 1,2-ethylene, 1,3-propylene, 1,4-butylene, hexamethylene, octamethylene, decamethylene, dodecamethylene, tetradecamethylene, hexadecamethylene, octadecamethylene, nonadecamethylene and especially methylene. The variable B comprises preferably 1 to 10 and especially 1 to 4 carbon atoms.

The primary and secondary amines as a reaction partner for the polycarboxylic acids to form component (K4) are typically monoamines, especially aliphatic monoamines. These primary and secondary amines may be selected from a multitude of amines which bear hydrocarbon radicals which may optionally be bonded to one another.

These parent amines of the oil-soluble reaction products of component (K4) are usually secondary amines and have the general formula $HN(R^8)_2$ in which the two variables $R^8$ are each independently straight-chain or branched $C_{10}$- to $C_{30}$-alkyl radicals, especially $C_{14}$- to $C_{24}$-alkyl radicals. These relatively long-chain alkyl radicals are preferably straight-chain or only slightly branched. In general, the secondary amines mentioned, with regard to their relatively long-chain alkyl radicals, derive from naturally occurring fatty acid and from derivatives thereof. The two $R^8$ radicals are preferably identical.

The secondary amines mentioned may be bonded to the polycarboxylic acids by means of amide structures or in the form of the ammonium salts; it is also possible for only a portion to be present as amide structures and another portion as ammonium salts. Preferably only few, if any, free acid groups are present. The oil-soluble reaction products of component (K4) are preferably present completely in the form of the amide structures.

Typical examples of such components (K4) are reaction products of nitrilotriacetic acid, of ethylenediaminetetraacetic acid or of propylene-1,2-diaminetetraacetic acid with in each case 0.5 to 1.5 mol per carboxyl group, especially 0.8 to 1.2 mol per carboxyl group, of dioleylamine, dipalmitinamine, dicoconut fatty amine, distearylamine, dibehenylamine or especially ditallow fatty amine. A particularly preferred component (K4) is the reaction product of 1 mol of ethylenediaminetetraacetic acid and 4 mol of hydrogenated ditallow fatty amine.

Further typical examples of component (K4) include the N,N-dialkylammonium salts of 2-N',N'-dialkylamidobenzoates, for example the reaction product of 1 mol of phthalic anhydride and 2 mol of ditallow fatty amine, the latter being hydrogenated or unhydrogenated, and the reaction product of 1 mol of an alkenylspirobislactone with 2 mol of a dialkylamine, for example ditallow fatty amine and/or tallow fatty amine, the last two being hydrogenated or unhydrogenated.

Further typical structure types for the component of class (K4) are cyclic compounds with tertiary amino groups or condensates of long-chain primary or secondary amines with carboxylic acid-containing polymers, as described in WO 93/18115.

Sulfocarboxylic acids, sulfonic acids or derivatives thereof which are suitable as cold flow improvers of class (K5) are, for example, the oil-soluble carboxamides and carboxylic esters of ortho-sulfobenzoic acid, in which the sulfonic acid function is present as a sulfonate with alkyl-substituted ammonium cations, as described in EP-A 261 957.

Poly(meth)acrylic esters suitable as cold flow improvers of class (K6) are either homo- or copolymers of acrylic and methacrylic esters. Preference is given to copolymers of at least two different (meth)acrylic esters which differ with regard to the esterified alcohol. The copolymer optionally comprises another different olefinically unsaturated monomer in copolymerized form. The weight-average molecular weight of the polymer is preferably 50 000 to 500 000. A particularly preferred polymer is a copolymer of methacrylic acid and methacrylic esters of saturated $C_{14}$ and $C_{15}$ alcohols, the acid groups having been neutralized with hydrogenated tallamine. Suitable poly(meth)acrylic esters are described, for example, in WO 00/44857.

The cold flow improver or the mixture of different cold flow improvers is added to the middle distillate fuel or diesel fuel in a total amount of preferably 10 to 5000 ppm by weight, more preferably of 20 to 2000 ppm by weight, even more preferably of 50 to 1000 ppm by weight and especially of 100 to 700 ppm by weight, for example of 200 to 500 ppm by weight.

B4) Lubricity Improvers

Suitable lubricity improvers or friction modifiers are based typically on fatty acids or fatty acid esters. Typical examples are tall oil fatty acid, as described, for example, in WO 98/004656, and glyceryl monooleate. The reaction products, described in U.S. Pat. No. 6,743,266 B2, of natural or synthetic oils, for example triglycerides, and alkanolamines are also suitable as such lubricity improvers.

B5) Corrosion Inhibitors

Suitable corrosion inhibitors are, for example, succinic esters, in particular with polyols, fatty acid derivatives, for example oleic esters, oligomerized fatty acids, substituted ethanolamines, and products sold under the trade name RC 4801 (Rhein Chemie Mannheim, Germany) or HiTEC 536 (Ethyl Corporation).

B6) Demulsifiers

Suitable demulsifiers are, for example, the alkali metal or alkaline earth metal salts of alkyl-substituted phenol- and naphthalenesulfonates and the alkali metal or alkaline earth metal salts of fatty acids, and also neutral compounds such as alcohol alkoxylates, e.g. alcohol ethoxylates, phenol alkoxylates, e.g. tert-butylphenol ethoxylate or tert-pentylphenol ethoxylate, fatty acids, alkylphenols, condensation products of ethylene oxide (EO) and propylene oxide (PO), for example including in the form of EO/PO block copolymers, polyethyleneimines or else polysiloxanes.

B7) Dehazers

Suitable dehazers are, for example, alkoxylated phenol-formaldehyde condensates, for example the products available under the trade names NALCO 7D07 (Nalco) and TOLAD 2683 (Petrolite).

B8) Antifoams

Suitable antifoams are, for example, polyether-modified polysiloxanes, for example the products available under the trade names TEGOPREN 5851 (Goldschmidt), Q 25907 (Dow Corning) and RHODOSIL (Rhone Poulenc).

B9) Cetane Number Improvers

Suitable cetane number improvers are, for example, aliphatic nitrates such as 2-ethylhexyl nitrate and cyclohexyl nitrate and peroxides such as di-tert-butyl peroxide.

B10) Antioxidants

Suitable antioxidants are, for example substituted phenols, such as 2,6-di-tert-butylphenol and 6-di-tert-butyl-3-methylphenol, and also phenylenediamines such as N,N'-di-sec-butyl-p-phenylenediamine.

B11) Metal Deactivators

Suitable metal deactivators are, for example, salicylic acid derivatives such as N,N'-disalicylidene-1,2-propanediamine.

B12) Solvents

Suitable solvents are, for example, nonpolar organic solvents such as aromatic and aliphatic hydrocarbons, for example toluene, xylenes, white spirit and products sold under the trade names SHELLSOL (Royal Dutch/Shell Group) and EXXSOL (ExxonMobil), and also polar organic solvents, for example, alcohols such as 2-ethylhexanol, decanol and isotridecanol. Such solvents are usually added to the diesel fuel together with the aforementioned additives and coadditives, which they are intended to dissolve or dilute for better handling.

C) Fuels

The inventive additive is outstandingly suitable as a fuel additive and can be used in principle in any fuels. It brings about a whole series of advantageous effects in the operation of internal combustion engines with fuels. Preference is given to using the inventive quaternized additive in middle distillate fuels, especially diesel fuels.

The present invention therefore also provides fuels, especially middle distillate fuels, with a content of the inventive quaternized additive which is effective as an additive for achieving advantageous effects in the operation of internal combustion engines, for example of diesel engines, especially of direct-injection diesel engines, in particular of diesel engines with common-rail injection systems. This effective content (dosage) is generally 10 to 5000 ppm by weight, preferably 20 to 1500 ppm by weight, especially 25 to 1000 ppm by weight, in particular 30 to 750 ppm by weight, based in each case on the total amount of fuel.

Middle distillate fuels such as diesel fuels or heating oils are preferably mineral oil raffinates which typically have a boiling range from 100 to 400° C. These are usually distillates having a 95% point up to 360° C. or even higher. These may also be so-called “ultra low sulfur diesel” or “city diesel”, characterized by a 95% point of, for example, not more than 345° C. and a sulfur content of not more than 0.005% by weight or by a 95% point of, for example, 285° C. and a sulfur content of not more than 0.001% by weight. In addition to the mineral middle distillate fuels or diesel fuels obtainable by refining, those obtainable by coal gasification or gas liquefaction [“gas to liquid” (GTL) fuels] or by biomass liquefaction [“biomass to liquid” (BTL) fuels] are also suitable. Also suitable are mixtures of the aforementioned middle distillate fuels or diesel fuels with renewable fuels, such as biodiesel or bioethanol.

The qualities of the heating oils and diesel fuels are laid down in detail, for example, in DIN 51603 and EN 590 (cf. also Ullmann’s Encyclopedia of Industrial Chemistry, 5th edition, Volume A12, p. 617 ff.).

In addition to the use thereof in the abovementioned middle distillate fuels of fossil, vegetable or animal origin, which are essentially hydrocarbon mixtures, the inventive quaternized additive can also be used in mixtures of such middle distillates with biofuel oils (biodiesel). Such mixtures are also encompassed by the term “middle distillate fuel” in the context of the present invention. They are commercially available and usually comprise the biofuel oils in minor amounts, typically in amounts of 1 to 30% by weight, especially of 3 to 10% by weight, based on the total amount of middle distillate of fossil, vegetable or animal origin and biofuel oil.

Biofuel oils are generally based on fatty acid esters, preferably essentially on alkyl esters of fatty acids which derive from vegetable and/or animal oils and/or fats. Alkyl esters are typically understood to mean lower alkyl esters, especially $C_1$-$C_4$-alkyl esters, which are obtainable by transesterifying the glycerides which occur in vegetable and/or animal oils and/or fats, especially triglycerides, by means of lower alcohols, for example ethanol or in particular methanol (“FAME”). Typical lower alkyl esters based on vegetable and/or animal oils and/or fats, which find use as a biofuel oil or components thereof, are, for example, sunflower methyl ester, palm oil methyl ester (“PME”), soya oil methyl ester (“SME”) and especially rapeseed oil methyl ester (“RME”).

The middle distillate fuels or diesel fuels are more preferably those having a low sulfur content, i.e. having a sulfur content of less than 0.05% by weight, preferably of less than 0.02% by weight, more particularly of less than 0.005% by weight and especially of less than 0.001% by weight of sulfur.

Useful gasoline fuels include all commercial gasoline fuel compositions. One typical representative which shall be mentioned here is the Eurosuper base fuel to EN 228, which is customary on the market. In addition, gasoline fuel compositions of the specification according to WO 00/47698 are also possible fields of use for the present invention.

The inventive quaternized additive is especially suitable as a fuel additive in fuel compositions, especially in diesel fuels, for overcoming the problems outlined at the outset in direct-injection diesel engines, in particular in those with common-rail injection systems.

The invention is now illustrated in detail by the working examples which follow:

Experimental Section

A. General Test Methods a) Determination of the Amide or Imide Content by IR Spectroscopy The presence of amide or imide in a sample is examined by IR spectroscopy. The characteristic IR band for amide is at 1667±5 $cm^{-1}$, whereas the characteristic IR band of the imide is at 1705±5 $cm^{-1}$.

For this purpose, the samples were diluted 50% (m/m) in Solvesso and analyzed in a 29 μm $CaF_2$ cuvette.

b) Engine Test b) Engine test b1) XUD9 test—determination of flow restriction

The procedure was according to the standard stipulations of CEC F-23-01.

b2) DW10 test—determination of power loss as a result of injector deposits in the common-rail diesel engine To examine the influence of the additives on the performance of direct-injection diesel engines, the power loss was determined on the basis of the official test method CEC F-098-08. The power loss is a direct measure of formation of deposits in the injectors.

A direct-injection diesel engine with common-rail system according to test method CEC F-098-08 was used. The fuel used was a commercial diesel fuel from Halternann (RF-06-03). To synthetically induce the formation of deposits at the injectors, 1 ppm of zinc was added thereto in the form of a zinc didodecanoate solution. The results illustrate the relative power loss at 4000 rpm, measured during 12 hours of constant operation. The value "t0" indicates the power loss normalized (100%) to the value after 10 minutes; the value "t1" indicates the power loss normalized to the value after one hour.

c) Brief Sedimentation Test (BS Test)—Determination of Action as a Cold Flow Improver In the course of storage of diesel fuels in a storage or vehicle tank at temperatures below the cloud point (CP), precipitated paraffins can settle out. The paraffin-rich bottom phase which forms has a relatively poor cold performance, and can block filters of vehicles, thus leading to collapse of the delivery rate.

The BS test simulates and visually evaluates possible sedimentation in vehicle tanks. The CP and CFPP values of the diesel fuel phase enriched with paraffins obtained in the test are determined. The comparison of these values with those for the unsedimented fuel permits conclusions about the cold performance of the fuel. For this purpose, delta CP or delta CFPP values are determined.

In the test, the optionally additized diesel fuel (DF) to be tested is processed at −13° C. for a total of 16 h. It is assessed visually. Subsequently, 80% by volume of upper phase of the fuel is sucked out cautiously from the top. After heating and homogenizing the remaining 20% lower phase, the cloud point (CPCC) and the cold filter plugging point (CFPPCC) thereof are determined with apparatus known per se.

The procedure is to filter the amounts of sample required through a fluted filter (to DIN EN 116) to remove soil, coke constituents, water or other undissolved impurities. The sample vessel (scaled measuring cylinder) is filled with 550 ml of sample liquid. If required, the sample is admixed with additive. It is heated to 50° C. in a water bath. The sample vessel is removed from the water bath and dried. The sample is homogenized by inverting and shaking. The starting CP and CFPP values ("original") of portions are determined. The sample temperature is adjusted to close to 25° C. by standing under air.

The sample vessel containing 500 ml of sample is suspended in a liquid bath by means of a holding device. Heat treatment begins at 25° C. The sample is cooled to −13° C. within 2 h 40 min. The sample is stored at −13° C. for 13 h 20 min.

By means of a suction device, the sample is sucked out from the top down to a residual amount of 100 ml (20%). Sample movement and turbulence should be kept as low as possible. The sample vessel with the 20% lower phase remaining therein is heated to 50° C. The lower phase is homogenized and used to determine the final values of CP and CFPP (i.e. CPCC and CFPPCC).

d) Detection of the Betaine Structure

The betaine structure in inventive additives and the synthesis precursors thereof is detected by determination of mass using Matrix Assisted Laser Desorption/Ionization-Time Of Flight Mass Spectrometry (MALDI-TOF-MS). The analysis is effected under the following conditions:

The BIFLEX 3 instrument from Bruker and a UV laser of wavelength 337 nm are used. The laser power is increased until the ionization threshold of the ions is attained. The matrix consists of 20 g/l of dithranol in THF (ion-exchanged), using a polymer concentration of approx. 2 g/l in THF. The procedure is as follows: the matrix is mixed with the particular polymer in a ratio of 1:1, and 1 μl thereof is dried on the target ("dried-droplet technique"). The dried fractions are then dissolved in 20 μl of the matrix solution and finally analyzed. A total of 100 individual spectra are added up per measurement.

In addition, analysis is also effected by means of ESI-LC/MS (electrospray ionization liquid chromatography-mass spectrometry) in the solvent THF. For this purpose, the LTQ/FT (Thermo) MS system and the LC system consisting of HP 1100 bin pump, HP 1100 ALS and HP 1100 DAD are used. Approx. 10 mg of test substance are dissolved in 1 ml of THF and analyzed at room temperature. The resolution is 100 000.

e) Determination of the Motor Oil Compatibility of Diesel Fuels (DF)

The determination was effected by the methods in the catalog of criteria compiled by the Deutsche Wissenschaftliche Gesellschaft für Erdöl, Erdgas and Kohle e.V. (DGMK) for the testing of lubricity additives in diesel fuels (DGMK Report 531)

In the fuel system of diesel vehicles, it is possible that small amounts of motor oil get into the diesel fuel circuit. In some cases, it has been observed that reactions occurred between motor oil constituents and the additives present in diesel fuels, and led to blockages of fuel filters and hence to the failure of vehicles. Therefore, a test method was developed, with the aid of which reactions between motor oil and diesel fuel additives which would lead to filter blockages are recognized and assessed.

The additive to be tested is mixed with the same amount of the stipulated motor oil and conditioned at 90° C. over three days. After this conditioning, the mixture is diluted with diesel fuel and mixed, and assessed with the aid of the SEDAB test (DGMK Report 531, appendix II-A). The results from both tests permit a statement about the "motor oil compatibility" of the diesel fuel additive to be tested.

Equipment and Test Media:

500 ml Erlenmeyer flask with NS19 ground glass stopper
alpha-methylnaphthalene
diesel fuel which passes the SEDAB test impeccably
motor oil (CEC Reference Lube RL-189, SAE 15W-40)

The DF provided for performance of the test and the motor oil should be assessed with the aid of the SEDAB test before the first use thereof. For this purpose, 10 g of motor oil are dissolved in 500 ml of DF. To improve the solubility, it may be necessary to add 10 ml of alpha-methylnaphthalene and repeat the homogenization. This mixture is assessed immediately in the SEDAB test. When the mixture is filterable impeccably, the DF can be used for the performance of the testing.

10 g of motor oil and 10 g of the additive to be tested are each weighed into a 500 ml Erlenmeyer flask, and then homogenized by tilting the flask. In the case of poor miscibility, 10 ml of alpha-methylnaphthalene are additionally added and the mixture is homogenized again. This mixture is closed with a glass stopper and conditioned at a temperature of 90° C. in a drying cabinet for three days.

After conditioning, the mixture is allowed to cool at room temperature for one hour and assessed visually for any deposits, turbidity, gel formation, etc. The mixture is made up to 500 ml with diesel fuel and mixed thoroughly. It is assessed visually. Should deposits have formed, they should be suspended by vigorous shaking before the performance of the SEDAB test. After standing for two hours, the mixture is assessed visually again and then filtered through a 0.8 μm filter at a pressure differential of 800 mbar (see SEDAB test method). The total amount has to be filterable within the fixed time.

In the case of occurrence of deposits, turbidity, gel formation and/or poor filterability in the SEDAB test, the additive cannot be classified as motor oil-compatible. In the case of good filterability and impeccable visual appearance, the additive can be classified as motor oil-compatible.

Specifications for the SEDAB Test:

500 ml of a pretreated DF are sucked through a membrane filter. The time in seconds needed for this volume to filter at 20±2° C. and 200 hPa (i.e. pressure differential approx. 800 hPa) is determined. When this is more than two minutes, the amount of filtrate present after two minutes is noted.

Instruments/materials required

- Membrane filter: from Sartorius, made of cellulose nitrate, white, smooth, diameter 50 mm, pore size 0.8 μm.
- Filtration apparatus: filtration unit with 500 ml funnel: Sartorius SM 16 201
- Suction bottle: capacity 1000 ml
- Vacuum system: e.g. constant-vacuum TOM-VAC 1 Automatic Zerosystem with a minimum pressure of 200 hPa.
- Drying cabinet for heat treatment at 90±3° C., without air circulation
- Tweezers
- Glass Petri dish, diameter approx. 125 mm, with acceptable lid
- Sample vessel: measuring cylinder (capacity 500 ml) with glass joint and stopper.

To prepare the sample, the sample vessel of the original fuel sample is shaken with 20 vertical strokes. The sample is left to stand at room temperature for 16 hours. Immediately before the measurement, the fuel is homogenized once again by shaking (10 strokes) and introduced into the 500 ml funnel of the test apparatus.

The membrane filters are conditioned at 90±3° C. for a half hour in a drying cabinet and then stored in a desiccator until use. The correspondingly prepared membrane filter is placed into the filtration apparatus. The 500 ml funnel is filled with the entire sample (500 ml) and then a pressure of 200 hPa (absolute, corresponds to pressure differential approx. 800 hPa) is immediately applied. It should be ensured that no fuel sample is poured in thereafter. The filtration time is reported rounded to full seconds. If a filtration time of two minutes is exceeded without the entire sample being filtered, the test is ended and the volume of the fuel which has passed through to that point is measured. In this case, the result is reported as ">2 minutes" and the amount of sample (ml) filtered by the time the test was stopped. When the filtration time of the sample is more than two minutes, a corresponding specimen should be heated to 50° C. for 30 minutes and then filtered. If the test result is again above two minutes, the total soil content of the fuel should be determined to DIN 51 419.

After the filtration, funnel and filter are rinsed with n-heptane and then with petroleum spirit (40/80) to free them of DF. The membrane filter is cautiously removed from the filter plate with tweezers, placed into a clean Petri dish and dried in a drying cabinet at 90±3° C. with the lid half-open for 30 minutes. Thereafter, the Petri dish is placed into the desiccator for cooling for at least 15 minutes.

Samples which are filterable within two minutes by the above-described process are classified as "uncritical" with regard to the present test method. Diesel fuels which are not filterable within this time should be classified as "critical" and can lead to filter blockages in vehicles and at filling stations. In the case of samples with critical behavior, the membrane filter should be studied optically (microscopically) or by means of infrared spectroscopy for the cause of the blockage.

B. Preparation and Analysis Examples

Reactants used:

PIBSA: Mw=1100; hydrolysis number=85 mg KOH/g
DMAPA: Mw=102.18
Styrene oxide: Mw=120.15
Acetic acid: Mw=60.05

Preparation Example 1

Synthesis of an Inventive Acid-Free Quaternized Succinamide (PIBSA/DMAPA/styrene oxide; amidation at 40° C.)

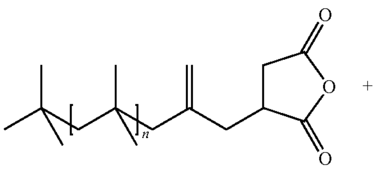

-continued

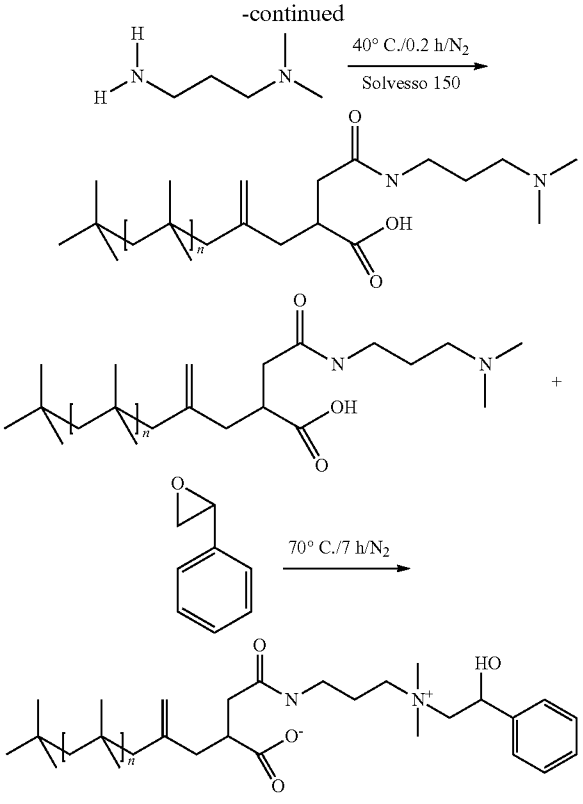

(A)

386.8 g (0.35 mol) of polyisobutenesuccinic anhydride (PIBSA 1000) are dissolved in 176 g of Solvesso 150 in a 2-liter four-necked flask at room temperature under a gentle N2 stream. After the addition of 29.9 g (0.29 mol) of 3-dimethylamino-1-propylamine (DMAPA), the reaction temperature rises to 40° C. The solution is stirred at 40° C. for 10 minutes. Subsequently, 34.2 g (0.29 mol) of (1,2-epoxyethyl) benzene are added, which is followed by a further reaction time of 7 hours at 70° C. under N2. The solution is finally adjusted to an active ingredient content of 50% with 274.9 g of Solvesso 150.

By IR analysis, it was possible to detect the formation of the inventive amide addition product (A).

By means of ESI-LC/MS and MALDI-TOF-MS, the betaine structure of (A) was determined experimentally.

Preparation Example 2 (Comparison)

Synthesis of an Acid-Containing Quaternized Succinimide (PIBSA/DMAPA/Styrene Oxide/Acetic Acid) Analogously to WO 2006/135881

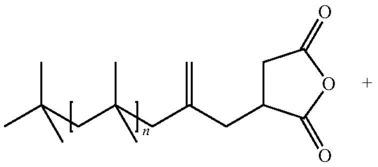

-continued

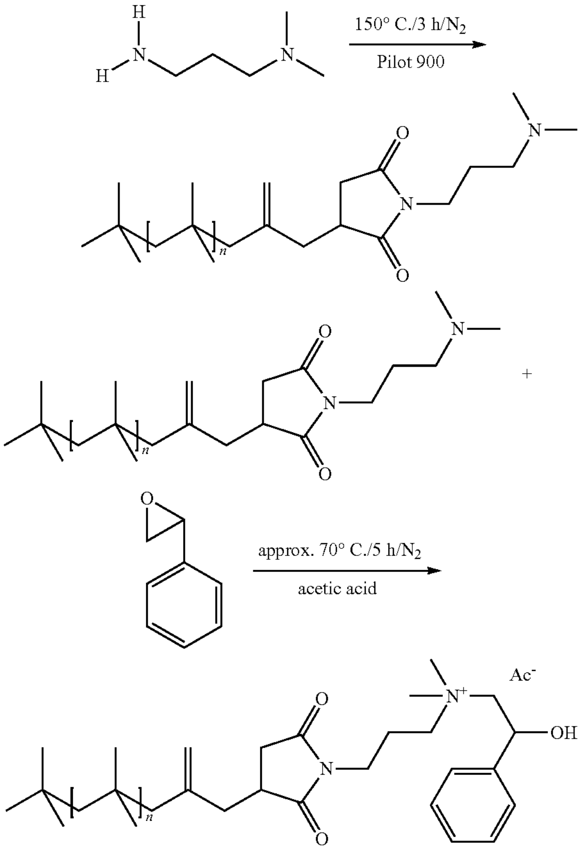

(B)

The overall experiment is performed under a gentle N2 stream. The initial charge of PIBSA 1000 (481.61 g) and Pilot 900 oil (84.99 g) is stirred at 110° C. Then DMAPA (37.28 g) is metered in at 110-115° C. within 42 minutes. A slightly exothermic reaction is observed. Subsequently, the mixture is heated to 150° C. and stirred at 150° C. for 3 h to remove water of reaction. The mixture is then cooled to room temperature, and successively admixed with MeOH (152 g), acetic acid (21.91 g) and styrene oxide (43.84 g). The mixture is then stirred at reflux (67-69° C.) for 5 h. After standing at 30-35° C. overnight, the mixture is concentrated by distillation (1 h/6 mbar/36° C. oil bath). The final weight of 661.1 g is adjusted to an active ingredient content of 50% with Pilot 900 oil (493.07 g).

By IR analysis, it was possible to detect the formation of the imide (B).

By means of ESI-LC/MS and MALDI-TOF-MS, the absence of a betaine structure in (B) was demonstrated experimentally.

C. Use Examples

In the use examples which follow, the additives are used either as a pure substance (as synthesized in the above preparation examples) or in the form of an additive package. The following packages were used:

M2450: Inventive additive package

| Additive | Proportion (%) |
|---|---|
| Product according to Prep. Ex. 1 | 48.06 |
| Dehazer | 0.92 |
| Antifoam | 1.11 |
| Solvesso 150 | 25.88 |
| Pilot 900 | 24.03 |
| Sum | 100 |

M2452: Comparative additive package

| Additive | Proportion (%) |
|---|---|
| Product according to Prep. Ex. 2 | 48.06 |
| Dehazer | 0.92 |
| Antifoam | 1.11 |
| Solvesso 150 | 49.91 |
| Sum | 100 |

Use Example 1

Determination of the Additive Action on the Formation of Deposits in Diesel Engine Injection Nozzles a) XUD9 Tests Fuel used: RF-06-03 (reference diesel, Halternann Products, Hamburg)

The results are compiled in the table which follows:

| Ex. | Designation | Active ingredient dosage [mg/kg] | Active ingredient dosage in the fuel [mg/kg] | Flow restriction 0.1 mm needle stroke [%] |
|---|---|---|---|---|
| #1 | Blank value | — | — | 61 |
| #2 | Additive according to preparation example 1 | 60 | 30 | 4.2 |

b) DW10 Test

The test results are shown in FIG. 1. The t0 values are plotted therein.

It is found that, at the same dosage (100 mg/kg of active ingredient, i.e. 200 ppm of preparation example 1), the inventive amide additive (rhombuses) and the imide comparative additive (triangles) significantly reduce the power loss observed for unadditized fuel (squares), although the inventive additive stabilizes the remaining power loss in the region of about 0.5% over the entire test duration, i.e. 99.5% of the original maximum engine power is maintained. With the corresponding comparative additive, however, only a power of 98.5% of the original maximum engine power is maintained.

Use Example 2

Determination of the Low-Temperature Properties—Brief Sedimentation Test

Commercially available winter DF was additized in the manner specified in the table below with additive according to preparation example 1 (#3) and additive according to preparation example 2 (#2), and also with additive package M2450 (#5) or M2452 (#4), and subjected to a BS test. The comparison (#1) used was DF with cold flow improver additive without amide and imide.

The test fuel used was diesel fuel from Bayernoil, (CP −6.5° C.).

All fuel samples (#1 to #5) were additionally additized with commercial middle distillate cold flow improver (MDFI) and wax antisettling additive (WASA).

It can be inferred from the test data compiled in the table which follows that the delta CP and CFPPCC values of the DFs additized in accordance with the invention are significantly improved compared to the imide-containing DFs. The amide additization can thus significantly improve the cold performance of the DFs.

| #1 | | #2 | | #3 | | #4 | | #5 | |
|---|---|---|---|---|---|---|---|---|---|
| — | | 130 ppm | | 130 ppm | | 270.5 ppm | | 270.5 ppm | |
| — | | | | | | M 2452 | | M 2450 | |
| — | | Comparison (Prep. Ex. 2) | | Invention (Prep. Ex. 1) | | Comparison (Prep. Ex. 2) | | Invention (Prep. Ex. 1) | |
| CP | CFPP | CP | CFPP | CP | CFPP | CP | CFPP | CP | CFPP |
| −6.5 | −27 | | −27 | | −27 | | −27 | | −27 |
| CPCC | CFPPCC | CPCC | CFPPCC | CPCC | CFPPCC | CPCC | CFPPCC | CPCC | CFPPCC |
| −3.3 | −20 | −3.8 | −21 | −6.2 | −28 | −1.8 | −20 | −6.1 | −28 |
| Delta CP | — | Delta CP | — | Delta CP | — | Delta CP | — | Delta CP | — |
| 3.2 | — | 2.7 | — | 0.3 | — | 4.7 | — | 0.4 | — |

CFPP: CFPP of the overall fuel
CFPPCC: CFPP of the lower phase
CPCC: CP of the lower phase
Delta CP: Difference from the CP of the fuel additized only with cold flow improver without addition of preparation example 1 or 2

Use Example 3

Determination of Motor Oil Compatibility

The determination was effected according to the specifications of DGMK Report 531.

Motor oil used: Wintershall 14W40 Multi Record Top

Diesel fuel (DF) used: RF-06-03 (reference diesel, Halternann Products, Hamburg)

The additive to be tested is mixed with the same amount of mineral oil (10 g each time), conditioned at 90μ C. for 3 days and assessed visually in the course thereof. Subsequently, the mixture is made up to 500 ml with diesel fuel, mixed and assessed with the aid of the SEDAB filtration test (likewise defined in DGMK Report 531).

The results are compiled in the table which follows:

| Test # | Product[a] (from preparation ex. X) | Visual 72 h/90° C. | Solubility in DF | Filtration |
|---|---|---|---|---|
| 1 | 2 (comparison) | solid (fail) | turbid, insoluble | fail |
| 2 | 1 (invention) | liquid (pass) | soluble | pass |

[a]since both products comprised different types of solvent (Solvesso 150 or Pilot 900) as a result of the synthesis, they were admixed with the same amount of the other solvent in each case before performance of the test, so as to give identical test conditions.

Use Example 4

Determination of the Effect of IDIDs

The determination was effected in a passenger vehicle operating test. Commercial diesel fuel (DF) EN590 was additized (with customary DF additives). The additive to be tested (inventive additive according to preparation example 1) was added to the EN590 DF. For comparison, commercial EN590 fuel which has not been admixed with an inventive additive was used. After the engine test had ended, the injectors were checked for deposits. A surprisingly clear positive effect on IDIDs is observed.

Test Procedure:

A passenger vehicle with common-rail injectors (magnet type), in which injector deposits had been found, was used for evaluation of the additive for removal of these internal injector deposits.

The occurrence of brownish internal deposits in the injectors was detected by visual inspection of the solenoid coil face, of the valve plate in front of the face and of the valve seat face, and was also noticeable through rough and noisy engine running. It was likewise possible to infer from the readout data that the amount of the fuel volume injected into the cylinder deviated distinctly from the normal value.

The engine was first operated on the road with the tank filled with conventionally additized diesel without inventive additive, EN590 base fuel (50 liters, 750 km in mixed operation on freeways, other major roads and downtown). No improvement in the internal deposits was observed when the vehicle was operated with a tank filled with unadditized fuel (cf. table below).

In the next step, the tank was filled with the same EN590 base fuel, but which had been admixed with the inventive additive in a dosage of 120 mg/kg of active material. The car was run again for 750 km in mixed operation. The deposits after 750 km were distinctly reduced after this test operation with additized fuel, as was already detectable by softer, quieter engine operation. The readout data from the engine control unit also showed that the amounts of fuel injected declined to the target value.

After two tank fillings and operation over 1500 km with fuel additized in accordance with the invention, the brownish injector deposits had disappeared completely from the solenoid coil face, the valve plate in front of the face and the valve seat face, as was discernible visually after the injector had been opened.

These results illustrate clearly that the inventive additive completely removed internal injector deposits (IDIDs) at low dosage. It can likewise be concluded from the test results that the additive is also capable of preventing the formation of IDIDs even at low dosage rates. Furthermore, it was found that the inventive additive is capable of eliminating not only wax- or soap-like IDIDs but also solid, carbon-like polymeric deposits.

TABLE

| Status | Test km total | Test km with additized fuel | Engine running | Visual inspection (solenoid coil face) | Data from ECU | Result |
|---|---|---|---|---|---|---|
| Standard vehicle for field operation | 0 | 0 | rough, loud | severe brownish deposits | injected fuel volume outside target value | severe deposits (carbon-containing) |
| 1st tank filling + running with unadditized fuel (EN590 base fuel) | 750 | 0 | rough, loud | severe brownish deposits | injected fuel volume outside target value | no improvement, severe deposits (carbon-containing) |
| 1st tank filling + running with additized fuel (dosage 120 mg/kg) | 1500 | 750 | quieter | reduced deposits | injected fuel volume within target value | reduced deposits |
| 2nd tank filling + running with additized fuel (dosage 120 mg/kg) | 2250 | 1500 | gentle, quiet | deposits completely disappeared | injected fuel volume within target value | deposits completely disappeared |

Reference is made explicitly to the disclosure of the publications cited herein.

The invention claimed is:

1. A method for reducing or preventing deposits in an injection system of a diesel engine, the method comprising adding a deposit reducing or deposit preventing effective amount of a quaternized nitrogen compound to a diesel engine in need thereof, wherein said quaternized nitrogen compound is a quaternized nitrogen compound prepared by a process comprising:

a) reacting an anhydride compound derived from a polycarboxylic acid, or a dimeric form thereof having two acid anhydride groups, with a compound comprising (i) a group comprising oxygen or nitrogen wherein the group is reactive with an anhydride, and (ii) a quaternizable amino group, to form a product, and b) quaternizing the product from a) to obtain the quaternized nitrogen compound, wherein the anhydride compound comprises a hydrocarbyl substituent having a number-average molecular weight (Mn) in a range from about 200 to 20 000;

wherein the quaternized nitrogen compound has a formula selected from the group consisting of formulae Ia-1, Ia-2, Ia-3, Ib-1, Ib-2 and Ib-3:

Ia-1

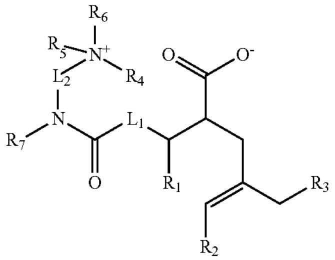

Ia-2

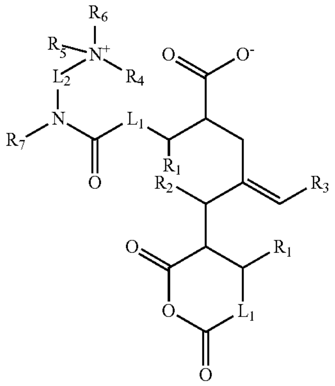

Ia-3

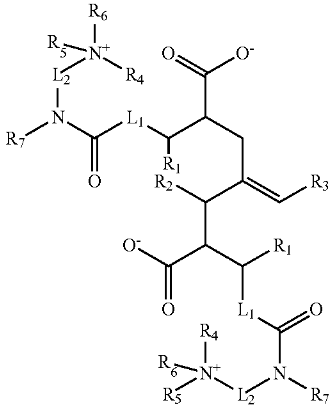

-continued

Ib-1

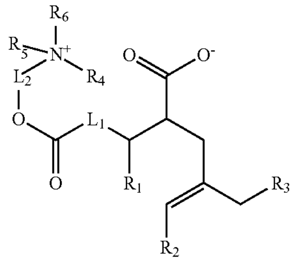

Ib-2

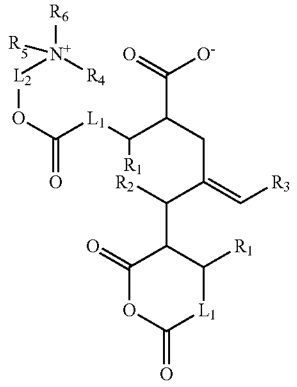

Ib-3

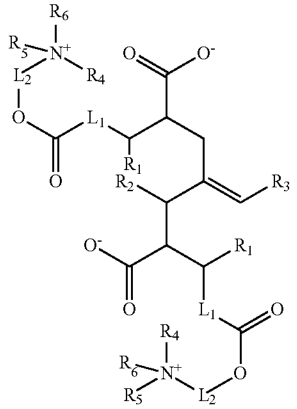

in which $R_1$ is H or a straight-chain or branched hydrocarbyl radical which may optionally be mono- or polysubstituted by hydroxyl, carboxyl, hydrocarbyloxy and/or an acyl radical, or has one or more ether groups in a hydrocarbyl chain;

$R_2$ is H or alkyl;

$R_3$ is hydrocarbyl;

at least one of $R_4$, $R_5$ and $R_6$ is a radical introduced by quaternization, and any of $R_4$, $R_5$ and $R_6$ that are radicals not introduced by quaternization are straight-chain or branched, cyclic hydrocarbyl radicals which are optionally mono- or polysubstituted and optionally have one or more heteroatoms;

$R_7$ is H or a straight-chain or branched hydrocarbyl radical which may optionally be mono- or polysubstituted by hydroxyl, carboxyl, hydrocarbyloxy and/or an acyl radical, or has one or more ether groups in a hydrocarbyl chain, or $R_7$ together with one of $R_4$, $R_5$ and $R_6$ forms a bridge group;

$L_1$ is a chemical bond or a straight-chain or branched alkylene group; and $L_2$ is a straight-chain or branched alkylene group which optionally bears one or more heteroatoms or substituents.

2. The method of claim 1, wherein said method is for preventing or reducing internal diesel injector deposits of a direct injection diesel engine.

3. The method of claim 1, wherein said method is for preventing or reducing flow restriction in an indirect injection diesel engine as determined by the XUD 9 test method.

4. The process of claim 1, wherein the anhydride compound is a di-, tri- or tetracarboxylic anhydride.

5. The process of claim 1, wherein the anhydride compound is an anhydride of a $C_4$-$C_{10}$-dicarboxylic acid.

6. The process of claim 1, wherein the anhydride compound comprises a hydrocarbyl substituent having a number-average molecular weight (Mn) in a range from about 200 to 10 000.

7. The process of claim 1, wherein the compound reactive with an anhydride is a) a hydroxyalkyl-substituted mono- or polyamine having at least one quaternizable primary, secondary or tertiary amino group;

b) a straight-chain or branched, cyclic, heterocyclic, aromatic or nonaromatic polyamine having at least one primary or secondary amino group and having at least one quaternizable primary, secondary or tertiary amino group; or c) a piperazine.

8. The process of claim 7, wherein the compound reactive with an anhydride is a) a hydroxyalkyl-substituted primary, secondary or tertiary monoamine, or a hydroxyalkyl-substituted primary, secondary or tertiary diamine, or b) a straight-chain or branched aliphatic diamine having two primary amino groups; a di- or polyamine having at least one primary and at least one secondary amino group; a di- or polyamine having at least one primary and at least one tertiary amino group; an aromatic carbocyclic diamine having two primary amino groups; an aromatic heterocyclic polyamine having two primary amino groups; or an aromatic or nonaromatic heterocycle having one primary and one tertiary amino group.

9. The process of claim 1, wherein the quaternizing agent is an epoxide.

10. The process of claim 9, wherein the quaternizing is performed without adding an H+ donor.

11. The process of claim 1, wherein the reacting a) is performed at a temperature of less than about 80° C.

12. The process of claim 1, wherein the reacting a) is performed over a period of 1 to 120 minutes.

13. The process of claim 1, wherein the quaternizing b) is performed at a temperature in a range from 40 to 80° C.

14. The process of claim 1, wherein the quaternizing b) is performed over a period of 1 to 10 hours.

15. The process of claim 1, wherein the quaternizing b) is performed with a hydrocarbyl epoxide as a quaternizing agent in the absence of free acid.

16. The process of claim 1, wherein the reacting a), the quaternizing b), or both, is carried out in the absence of an organic protic solvent.

* * * * *